(12) United States Patent
Champagne

(10) Patent No.: US 6,187,250 B1
(45) Date of Patent: Feb. 13, 2001

(54) CONTINUOUS GEL CASTING METHOD AND APPARATUS

(75) Inventor: James T. Champagne, Vashon, WA (US)

(73) Assignee: James Champagne, Seattle, WA (US)

(*) Notice: Under 35 U.S.C. 154(b), the term of this patent shall be extended for 0 days.

(21) Appl. No.: 09/136,525

(22) Filed: Aug. 19, 1998

(51) Int. Cl.$^7$ .............................. G01N 27/28; B29C 39/16
(52) U.S. Cl. .......................... 264/495; 204/470; 204/620; 264/40.6; 264/145; 264/299; 425/144; 425/145; 425/174.4; 425/308; 425/371; 425/812
(58) Field of Search ................................. 264/299, 102, 264/494, 495, 496, 40.6, 145, 148; 425/174.4, 371, 364 R, 143, 144, 145, 308, 131.1, 812; 204/467, 469, 470, 619, 620, 621

(56) References Cited

U.S. PATENT DOCUMENTS

| | | | |
|---|---|---|---|
| 3,422,178 | * | 1/1969 | Junker et al. .......................... 425/371 |
| 4,594,064 | * | 6/1986 | Anderson .............................. 204/619 |
| 4,790,919 | * | 12/1988 | Baylor, Jr. ............................ 264/494 |
| 5,350,552 | * | 9/1994 | Ebata et al. ........................... 264/299 |

FOREIGN PATENT DOCUMENTS 60-203847 * 10/1985 (JP) ..................... 204/620

* cited by examiner

*Primary Examiner*—Mathieu D. Vargot
(74) *Attorney, Agent, or Firm*—Shanks & Herbert

(57) ABSTRACT

An apparatus and method which allows one skilled in the art to make either gradient or non-gradient slab gels continuously so that the produced gels are uniformly formed, polymerized and cut to a specific size as needed, in a mass-produced, assembly line manner.

28 Claims, 17 Drawing Sheets

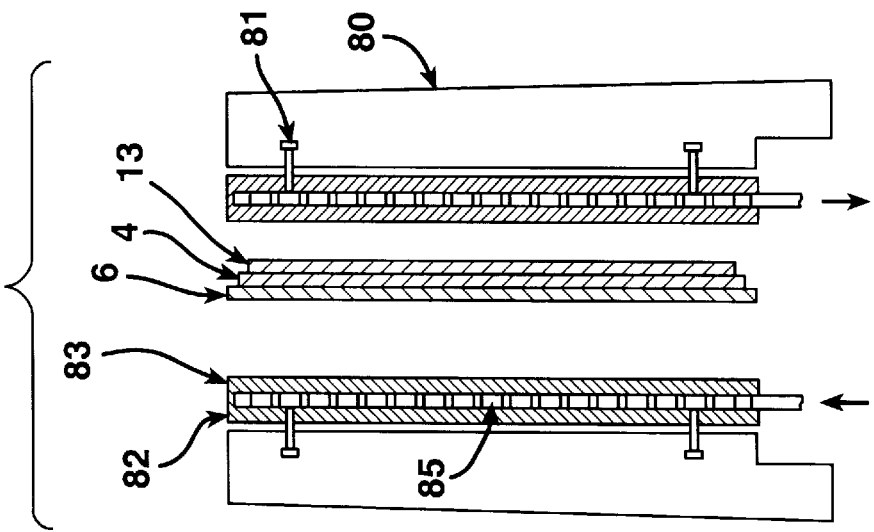
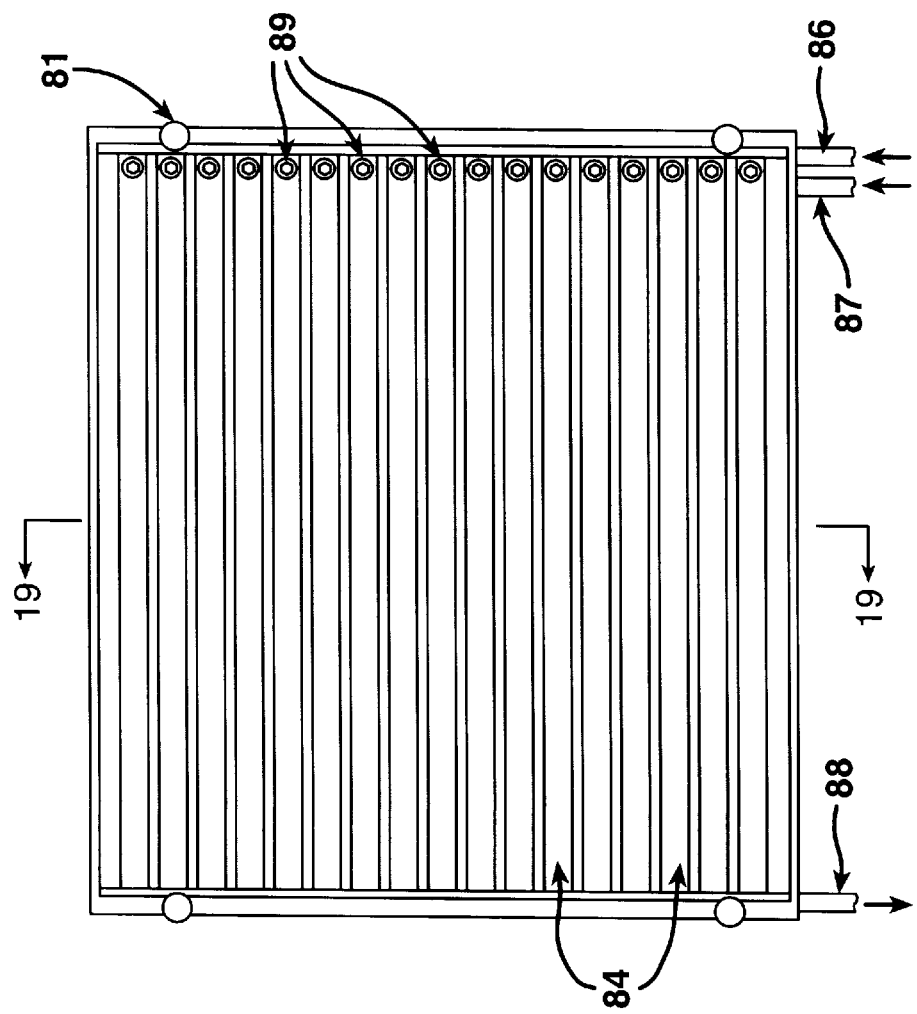

CONTINUOUS GEL CASTING METHOD AND APPARATUS

TECHNICAL FIELD AND INDUSTRIAL APPLICATION OF INVENTION

The invention relates to the production of acrylamide or other gels for use in separations of proteins, nucleic acids or other biological materials. The invention further relates to a continuous gel casting method and apparatus. In particular, the invention is intended to provide a method and apparatus for casting gels, and particularly, gradient gels, in a continuous manner as compared to the batch methods presently used.

BACKGROUND OF THE INVENTION

The separation of macromolecules through the use of gel electrophoresis has been common practice in biological laboratories for over twenty years. The technique is in even greater use in the last decade due to the tremendous explosion in protein analysis and the sequencing of genes. Since the late 1980's, rapid protein analysis and gene sequencing has become not only ubiquitous, but absolutely necessary for researchers. In particular, gels are often the starting points for new drug targets and also for sequencing as it relates to overall scientific endeavors such as the human genome project.

In general, electrophoresis gels can be either in a slab gel or tube gel form. For slab gels, the apparatus used to prepare them usually consists of two glass or plastic plates with a space disposed between them by means of a spacer or gasket material and the apparatus is held together by a clamping means so that the space created is closed on three sides and open at the top. A solution of unpolymerized gel, such as polyacrylamide, is poured into the space while in its liquid state. A means of creating wells or depressions in the top of the gel (such as a comb) in which to place samples is then placed in the space. The gel is then polymerized and becomes solid. After polymerization is complete, the comb device is removed and the gel, while still held within the plates, is then ready for use. Examples of such apparatus are well known and are described in U.S. Pat. No. 4,337,131 (Vesterberg), U.S. Pat. No. 4,339,327 (Tyler), U.S. Pat. No. 3,980,540 (Hoefer et al.), U.S. Pat. No. 4,142,960 (Hahn et al.), U.S. Pat. No. 4,560,459 (Hoefer), and U.S. Pat. No. 4,574,040 (Delony et al.). Tube gels are produced in a similar manner, however, instead of glass or plastic plates, glass capillary tubing is used to contain the liquid gel. It is important to note that each slab gel must be produced one at a time in this manner.

In addition to ordinary acrylamide gels, methods of making the composition of the gel vary along one or two directions, so called gradient gels have also been devised. Gradient gels are gels that have characteristics such as pH or pore size or percentage of crosslinked acrylamide which vary as a sample travels through the gel in one direction. A good general overview of the common method of preparing gradient gels is provided in Westermeier, *Electrophoresis in Practice,* VCH: New York, 1993, pp. 25–27, 174–177, and 197–214. In particular, *Westermeier* describes the pouring of a single linear pH gradient gel. It is even possible to construct gels that vary in two directions, such as pH from left to right across the slab while increasing in pore size from the top to the bottom of the slab. U.S. Pat. No. 5,071,531 (Soane) describes an apparatus for making such a gradient slab gel. In addition, U.S. Pat. No. 5,597,480 (Zhou) describes an apparatus which can be adapted to create a gradient slab gel.

Because of the tremendous need for faster and faster analysis of proteins and sequencing of genes due to their value as drug and disease targets in all aspects of biology, there exists a critical need for users to have access to hundreds or even thousands of gels for use in separations in a short period of time. Users, such as genomics companies, must be able to rely on gels that are produced quickly and inexpensively yet are absolutely consistent in their performance from batch to batch. To satisfy this need, a method of producing multiple gels in a batch manner on a large scale was needed.

A number of patents disclose methods for batch production of gels. U.S. Pat. No. 5,047,135 (Nieman) describes a modified slab gel apparatus where the gels are actually very thin wafers kept separate through the use of thin divider sheets. The multiple gels are all sandwiched together and run as one slab, but then may be peeled off and separately processed. Another method of producing a plurality of slab gels is disclosed in U.S. Pat. No. 5,520,790 (Chopas et al.), wherein a casting stand is described which can accommodate a number of separate gel molds held vertically. The individual gel molds can then be filled simultaneously from the bottom and can be ordinary gels or gradient gels via the use of a gradient former in combination with the apparatus. The article by P. G. Righetti, "Modern Aspects of Isoelectric Focusing: Two-Dimensional Maps and Immobilized pH Gradients," *Journal of Biochemical and Biophysical Methods,* 8:89–108 (1983), describes a gel casting method in which 20 gels are made concurrently for a single isoelectric focusing run. The gel casting method comprises pouring the gelling mixture into a loading trough, which is lowered into a tank partly filled with water. As the trough sinks to the bottom, the gelling mixture is displaced into tubes at the desired level. The gels are then allowed to polymerize in the tubes.

What is needed presently, is an apparatus which could allow one skilled in the art to make either gradient or non-gradient slab gels continuously so that the gels produced are uniformly formed, polymerized and cut to a specific size as needed, in a mass-produced, assembly line manner. The present invention accomplishes this goal and is described in specific detail below.

SUMMARY OF THE INVENTION

The present invention discloses an apparatus for the continuous casting of a gel by introducing the gel reaction mixture into a molding space and a casting manifold which encloses the molding space and provides a continuously moving, sealed molding space for holding the reaction mixture during gelation.

Specifically, the present invention describes a means of introducing a reaction (monomer) solution into a molding space or manifold in a controlled manner. The invention also describes a means of introducing the reaction solution in either a temporally or spatially varying manner so the final gel contains a concentration gradient.

Additionally, the present invention describes a casting manifold and within it a molding space to hold the reaction solution (gel) and initiators of polymerization without leaking at a maximum pressure of less than one atmosphere during the time it takes for the polymer to gel, but not necessarily complete polymerization. The invention also describes allowances for shrinkage of the gel of a few percent and a venting mechanism to displace entrained air in the mold space because air or other fluids can be entrained in the molding space in some applications where the gel is molded in a discontinuous fashion into a support cassette or backing or mask containing holes or spaces to be filled with gel. This air or other fluid is inadvertently carried into the molding space with the support cassettes or backing or masks as they are introduced into the casting manifold.

The invention further describes a controlled means of initiating the free radical polymerization process as the reaction mixture enters the mold space. In addition, it discloses methods to prevent premature polymerization when using chemical free radical initiators and catalysts requiring thorough mixing into the reaction mixture just prior to entering the mold space. The present invention allows ultraviolet free radical generation to occur through the use of a UV transparent window in the side of the mold cavity.

The present invention additionally discloses a means of controlling the reaction temperatures in the molding space during the polymerization, removing excess reaction heat and a means of removing the gels from the mold cavity.

BRIEF DESCRIPTION OF THE DRAWINGS

FIG. 18 shows the front view of a temperature control platen.

FIG. 19 shows the side cross-sectional view of a temperature control platen.

DETAILED DESCRIPTION AND PREFERRED EMBODIMENTS OF THE INVENTION

Figure 1:
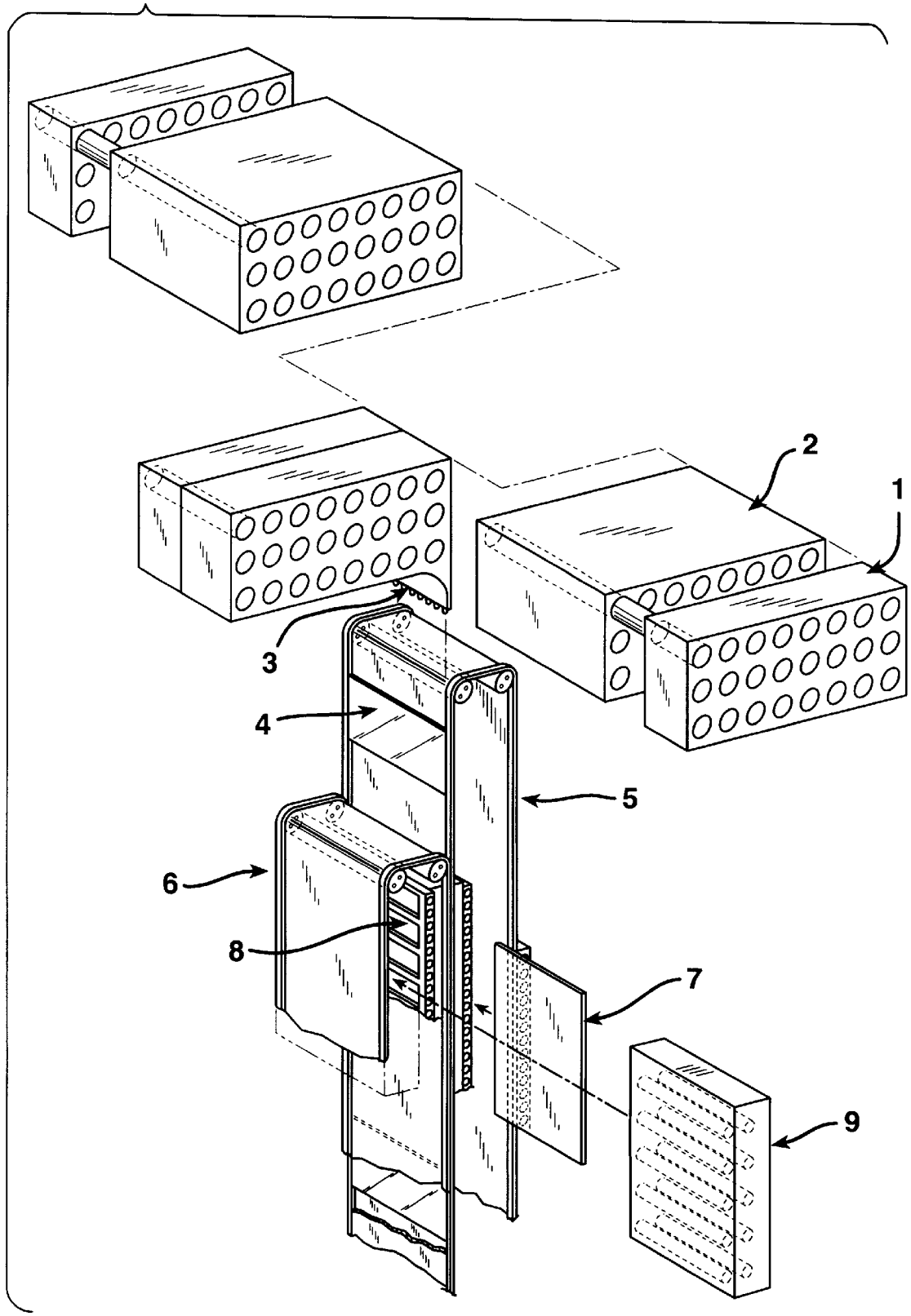
FIG. 1 shows a plan view and elevation and partial cross-sectional view of a schematic of the entire continuous gel casting apparatus and method.

According to the method and apparatus disclosed herein, pre-formulated solutions are prepared and delivered to a sealed casting manifold space in a controlled manner. FIG. 1 illustrates an overall orientation for the entire apparatus. Here we see the two halves of the reservoir cylinder block at the head of the apparatus. Each half consists of a top (1) and bottom section (2). When placed together, the reservoir cylinders empty into specific nozzles (3) which deliver the premixed gel solution onto a backing (4) which rides between a "support" belt (5) and a "gel-side" belt (6). The gel is sealed between these two polyester film or equivalent belts (approximately 0.005 mm to 1 mm in thickness) and travels in a horizontal orientation. The belts are kept sealed by pressure plates or "platens" (7) which may contain UV windows (8) that allow initiation of polymerization by a UV light source (9) in one embodiment. The apparatus is discussed in considerable detail below.

Figure 2:
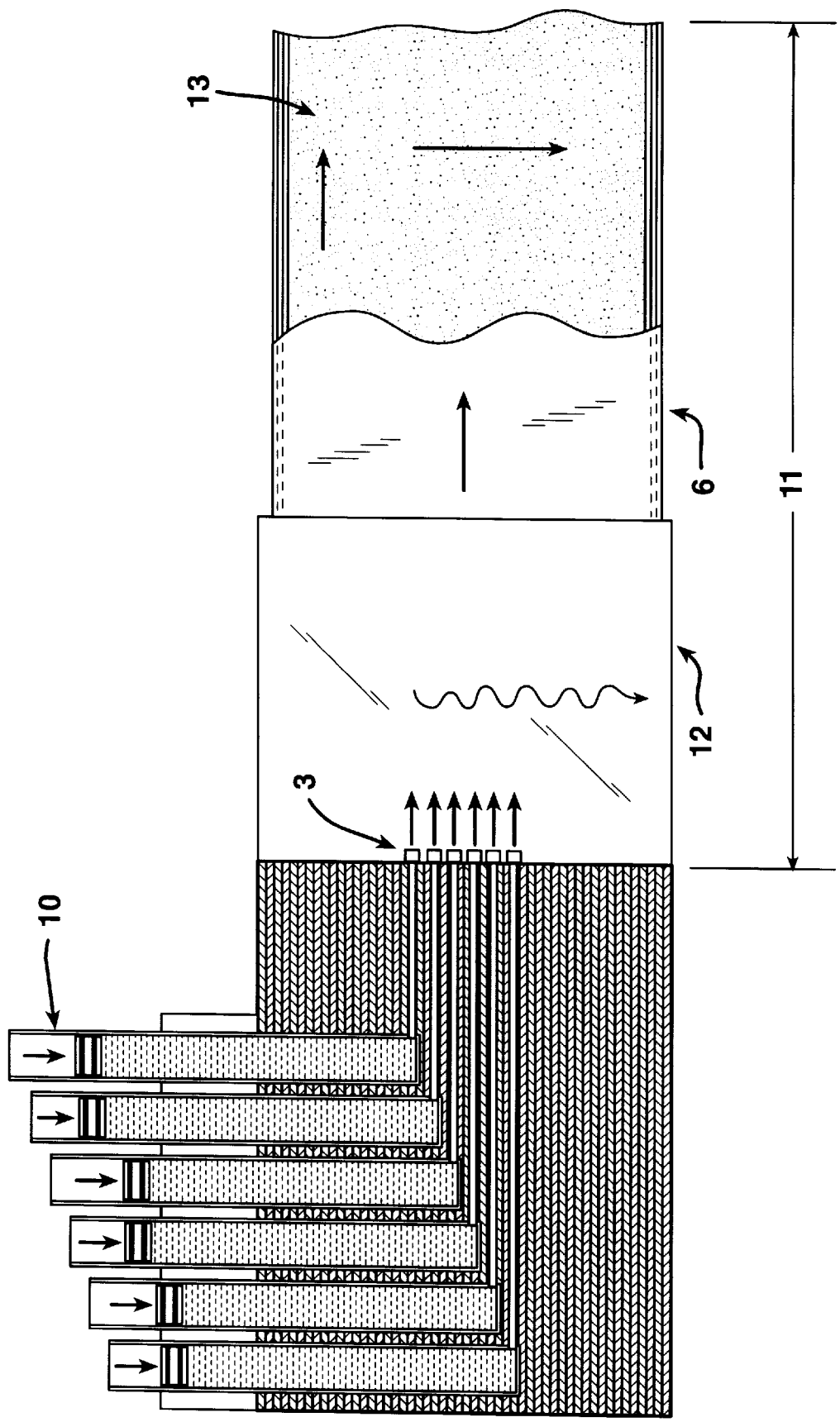
FIG. 2 shows a schematic representation of the gel being formulated in a gradient fashion on a backing and being transported down the belt.

Specifically, for the preparation of a gradient gel, the solutions are added in a temporally or spatially varied manner. The solutions may comprise premixed variable composition feedstock sources and gelation initiation components. FIG. 2 shows a cut-away view multi-chamber reservoir cylinder block with a plurality of incremental formulation reservoirs that deliver pre-formulated solutions through nozzles into one vertical edge of the molding space in order to create predetermined gradient conditions in a schematic fashion. The number of incremental formulation reservoirs is limited only by the ability to locate sufficient reservoir cavities (10) in a cylinder block with delivery pathways to the mold cavity that do not create significant pressure variations between reservoirs. The number of incremental formulation reservoirs should also be sufficient so as to allow for increment to increment diffusion after delivery to, and within, the mold cavity prior to gelation (11) in order to provide a smooth continuous compositional gradient in the finished gel without detectable stepwise compositional artifacts. These solutions are delivered to the sealed casting manifold or molding space from a plurality of incremental formulation reservoirs (10) at one vertical edge of the casting manifold space. The means for delivering the reaction solution to the molding space involves the use of a multi-chamber cylinder block and pistons, which allows the solutions to be delivered in a controlled and uniform rate. The multi-chamber reservoir cylinder block provides a means of supplying multiple separately or individually formulated streams of reaction mixture to the casting manifold through a series of nozzles (3) at one end of the molding space. The wavy line in the molding space (11) represents a possible gel concentration gradient. Also one face of the molding space is a UV transparent platen (12) or a platen which has UV windows within it to allow photochemical initiation of polymerization of the gel to begin. To the right of the UV transparent platen (12) in FIG. 2 is the back side of the "gel-side" belt (6) with the arrow indicating the direction of movement of the belts. To the right of the belt is illustrated the gel itself (13) with the horizontal arrow indicating the direction of movement of the gel and the vertical arrow representing a possible gel concentration gradient.

Figure 3:
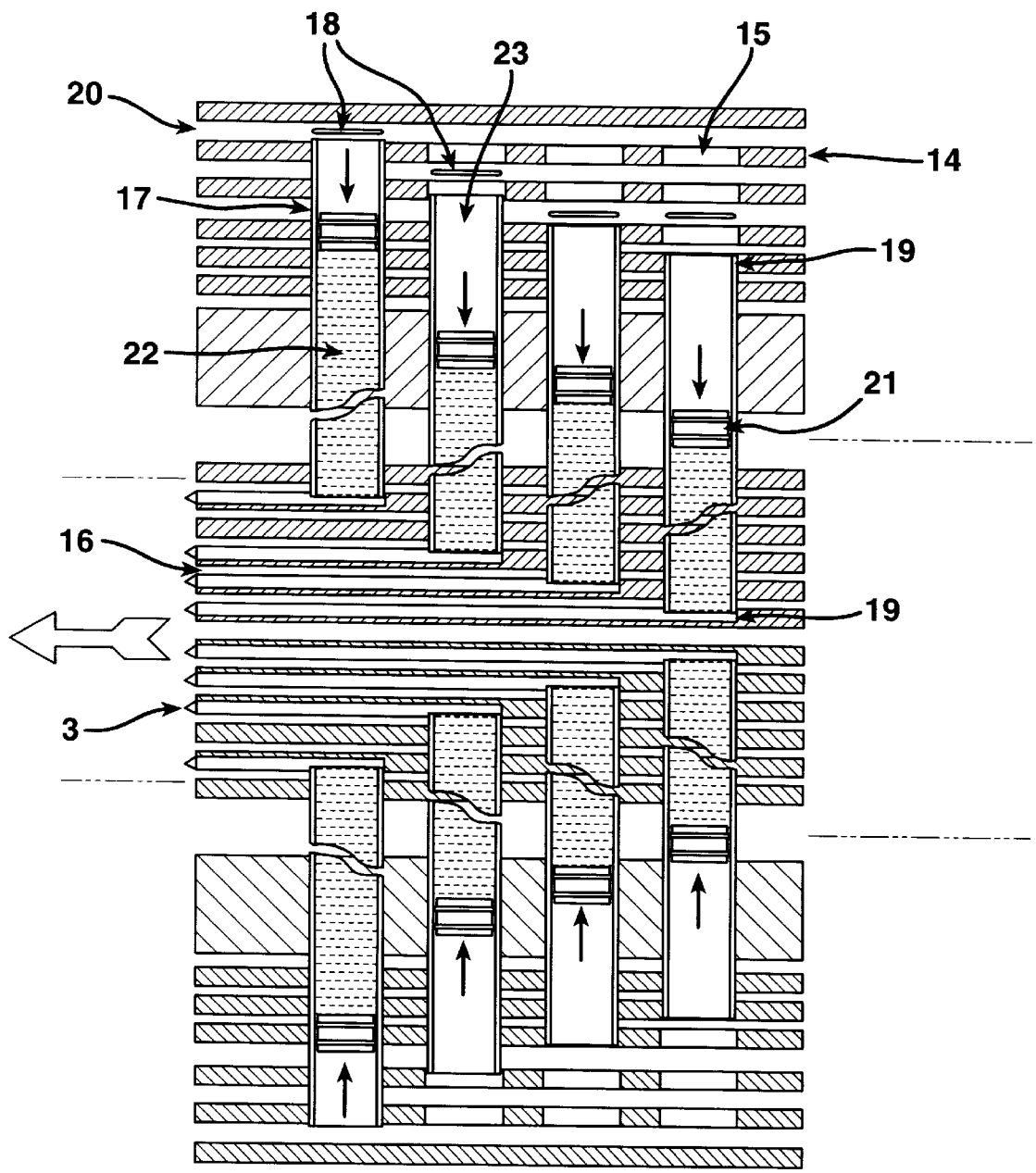
FIG. 3 shows an exploded cross-section of the multi-cylinder block reservoir

In a preferred embodiment, the cylinder block is built-up from a series of layered metal, plastic or composite laminations (14) and gaskets with an array of aligned holes (15) that define vertical cylindrical spaces or cavities when stacked together (FIG. 3). FIG. 3 illustrates an exploded view of a reservoir cylinder block. The image is oriented with the block cut in half lengthwise along both of the cylinder block halves (1,2) in FIG. 1. The laminations allow for the facile disassembly and re-assembly of the cylinder block for cleaning and can be variable in thickness. The laminations at the termination (top or bottom) of a particular cylinder should be of a thickness that allows for a horizontal delivery channel (16) to be formed within the lamination, or in a gasket between laminations, so as to provide the required incremental vertical dimension needed to accommodate the number of delivery nozzles over the total vertical dimension of the gradient. Those laminations within the cylinder block that do not provide horizontal delivery channels (i.e. above or below the vertical zone that contains the mold cavity and below or above the opposite ends of any cylinders) can be of whatever thickness is convenient for manufacturing and for disassembly or re-assembly. Each cylinder has a glass or plastic column (17) inserted with O-ring seals (18) at the top and bottom of said column that terminate the cylinder, closing the cylinder against specific layers (top & bottom) of the block and defining a primary reservoir. Each primary reservoir terminates at a different pair of laminations (one at the inlet or fluid supply end and one at the outlet or delivery end of the reservoir). Horizontal inlet & outlet channels (16) are provided in the "terminal" layers that connectively attach each glass, or plastic, primary reservoir to a common fluid supply (inlet channel) to provide positive hydraulic pressure (20) and each glass or plastic primary reservoir is provided, through the delivery (outlet) channel, one nozzle (3) at the casting manifold. A drive piston (21) is disposed within each primary reservoir and separates the primary reservoirs into an inlet and an outlet chamber with a reaction mix formula in the outlet chamber (22) (connected to the outlet) and a drive fluid (23) (typically water) in the inlet chamber. This inlet chamber is connected to a pump that supplies a uniform pressure to the primary reservoirs and a uniform flow rate for each primary reservoir. The large arrow on the left of the block in FIG. 3 illustrates the direction of the flow from the nozzles and the movement of the belts away from the reservoir cylinder block and molding space.

In a preferred embodiment (as shown in FIG. 3), the primary reservoirs in the manifold are arranged so that all the delivery channels that supply reaction mix formulations to the vertical nozzle array have their delivery channels at the same elevation as the nozzles. Those that supply reaction mix formula to the topmost one half of the vertical nozzle array are arranged so that their supply (inlet) channels are above the nozzle array and conversely, those that supply reaction mix formula to the bottommost one half of the vertical nozzle array are arranged so that their supply (inlet) channels are below the nozzle array. This allows more reservoirs to be located close to the mold space. The laminated cylinder block supports the glass, or plastic, columns disposed within them and provides resistance against the internal hydraulic pressure. In those applications such as the discontinuous casting into a support cassette or other structures containing holes or space, a means of measuring, calibrating and fine tuning the flow rates from each reservoir and to each nozzle is provided to ensure that the integral reaction formula volume to each nozzle over the complete course of a gel casting run does not vary by greater than 0.1% relative to the other reservoirs. This calibration will prevent the incremental composition from any reservoir/nozzle from distorting the gel gradient. In applications where the overall flow rate to the mold space is interrupted, such as the discontinuous casting into a support cassette or other structure containing holes or spaces, a smaller secondary constant pressure expansion cylinder (see FIG. 10) is optionally provided for each primary reservoir to act as a pressure and flow buffer to accommodate intermittent flow interruptions on a time scale of seconds that are associated with applications such as the discontinuous casting applications into a support cassette. This provision eliminates the need to make constant and complex adjustments to the overall flow rate or continuous casting line speed for these applications.

In an alternate embodiment, the pressure and flow-buffering chamber could use an elastomeric membrane or a piston to isolate the reaction mix from a constant pressure source on the opposite side of the piston or membrane. The total flow rate interruption that one must buffer against is much less than 1% of the total primary reservoir volume. One would calibrate the overall flow rate and casting line speed to the average flow rate, taking into account the "lost" volume due to the volume of the empty support itself. Of course, in the standard casting operation there is no need for this kind of buffering, where the polymerizing gel is a continuous ribbon.

Once the gel solutions are directed into the molding space, they are held for a time sufficient to initiate polymerization and allow shrinkage of the gel. The sealed manifold comprises two continuous flexible moving belts that are sealed together along their top and bottom edges to form two sides of the casting manifold with a fixed spacing between the two belts. In a preferred embodiment, the continuous belts are constructed from a resilient, flexible material. The pre-formulated solutions are introduced into the molding space between the two belts for gel formation. A gel backing or cassette acting as a secondary support means is comprised of a glass or plastic laminate is inserted by an insertion means into the molding space. The purpose of the secondary support means is to provide support to the polymerizing gel which is applied onto the gel backing in the molding space. The gel can adhere to the backing through surface tension properties and/or by adhesive properties of the gel mixture and backing surface. The flexible moving belts are affixed to a roller means for rotating, which allows the gel polymerized between the two belts to be moved through the apparatus for subsequent cutting and stacking on a continuous basis. Moreover, the belts are "sealed" on the upper and lower outer sides of the belts by pressing the belts together with two or more sets of opposable compression rollers that have a provision to adjust the level of pressure applied. At one end of the molding space, a plurality of nozzles from the multi-chamber cylinder block feed the pre-formulated solutions in a controlled manner at a uniform rate. The other end of the molding space is sealed by means of the solidifying polymer gel, which allows the gel to shrink under constant pressure. The belt speed corresponds to the rate at which the pre-formulated solutions are delivered, and depends upon the time required to allow for polymerization of the gel in the cavity under constant pressure. Upon completion of the polymerization process, the unsealing of the two belts permits the completed gels to be continually moved from the molding space into a cutting and stacking device for further processing.

Figure 4:
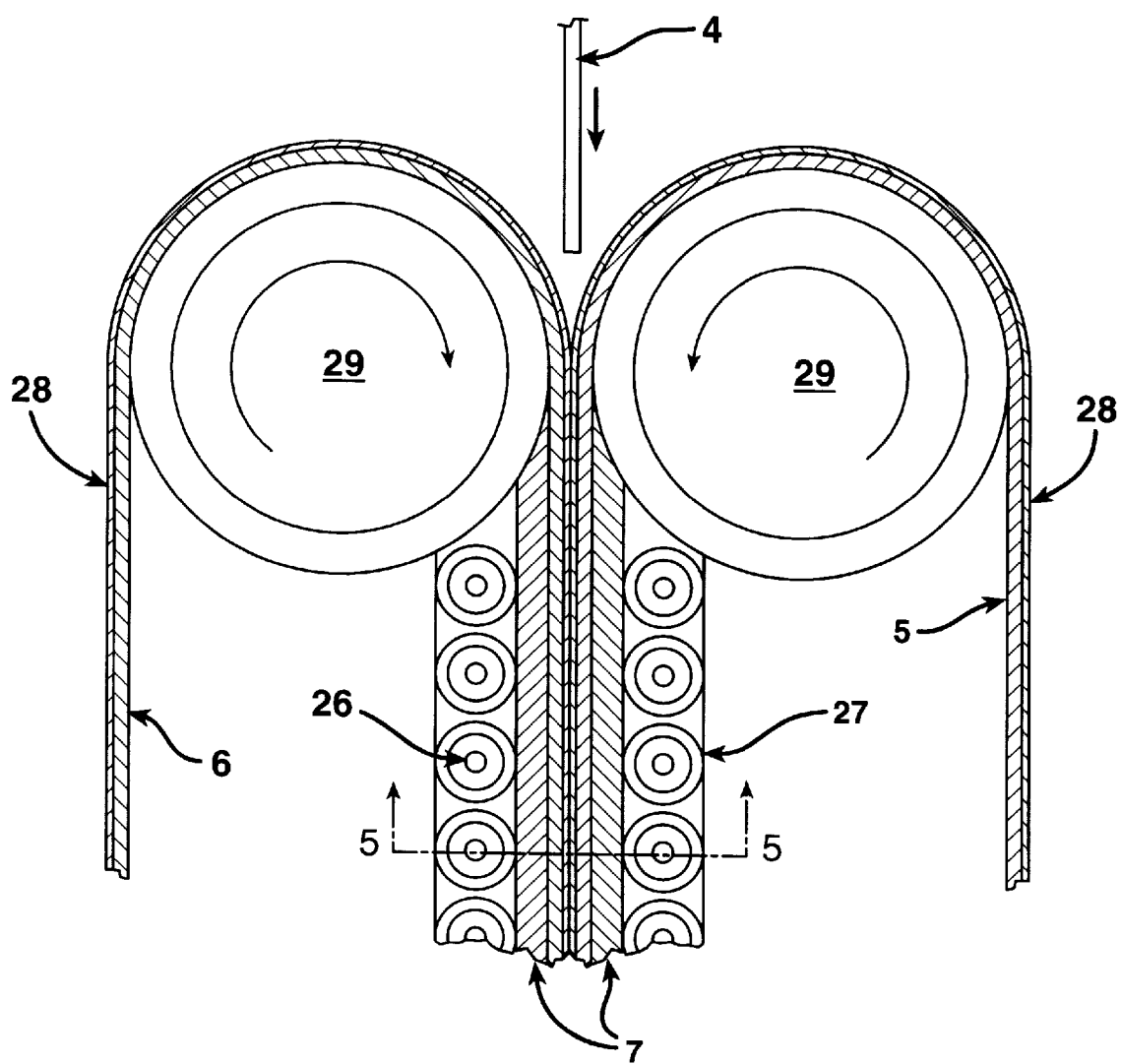
FIG. 4 shows in greater detail the drive wheels used in the casting apparatus.

FIG. 4 shows a plan view in greater detail of the apparatus used in the casting apparatus. The casting apparatus provides a means of creating a continuously moving, sealed molding space for maintaining the reacting gel solution at a modest pressure during the gelation process. In one embodiment, the upper and lower sides of this cavity are sealed when the support belt (5) that supports the gel backing (4) presses against the "gel-side" belt (6). In a preferred embodiment, the gel backing is a glass plate; it may also be plastic or some other laminate or composite. In an alternate embodiment, this sealing is made between the gel side belt (6) and the gel support backing side belt that have continuously mating surfaces (24) (hidden from view in FIG. 4) on their upper and lower sides that are pressed closed and create a pressure tight seal, up to one atmosphere or less of pressure as the belts enter a carefully spaced gap (25) (hidden from view in FIG. 4). Upper and lower sets of opposable compression rollers (26) and (27) (approximately 1 cm in height) which are mounted above and below the platens (7) (see FIG. 5) press on a stiff strip of material such as nylon corded neoprene (28), of the type used for timing belts. In a preferred embodiment, the continuously mating surfaces are comprised of flat elastomeric strips (24) composed of a flexible pliant material such as silicone rubber with a thickness varying from 0.01 to 1 mm. Said elastomeric strips are attached to the cavity side of the flexible continuous belts (5 & 6) at the upper and lower sides and backed up on the outside face of these flexible belts with a stiff strip of material such as nylon corded neoprene (28), of the type used for timing belts, of approximately 6 cm×10 cm (width and height) to provide a surface that can ride over the opposable compression roller sets and transfer sealing pressure to the mating surface elastomeric strips. This stiff backing strip can be pitched with teeth that match teeth on the roller sets providing accurate register between the continuous belt assembly and driven roller sets. FIG. 4 also shows two large drive rollers (29) which drive both belts (5 & 6) along the entire apparatus and maintain both belts at a matched and constant speed. The thickness of the gel must be carefully maintained during the gelation process. In a preferred embodiment, this is accomplished by reliance on the flexibility of the belts and their ability to deform to the exact shape and thickness of the mold cavity by internal manifold pressure of less than one atmosphere that presses the belts against the rigid platens or opposable compression rollers (26) & (27) on each side of the mold space. The thickness of the produced gel ranges from about 0.15 mm to about 5 mm (for protein analysis) and from about 0.05 mm to about 0.3 mm for DNA analysis. However, it may also vary depending on the reaction mixture and the type of gel to be produced. For example, an embodiment using embedded substrates for "in-gel" or zymogram assays the thickness can be limited to less than about 1 mm to conserve substrate.

Figure 5:
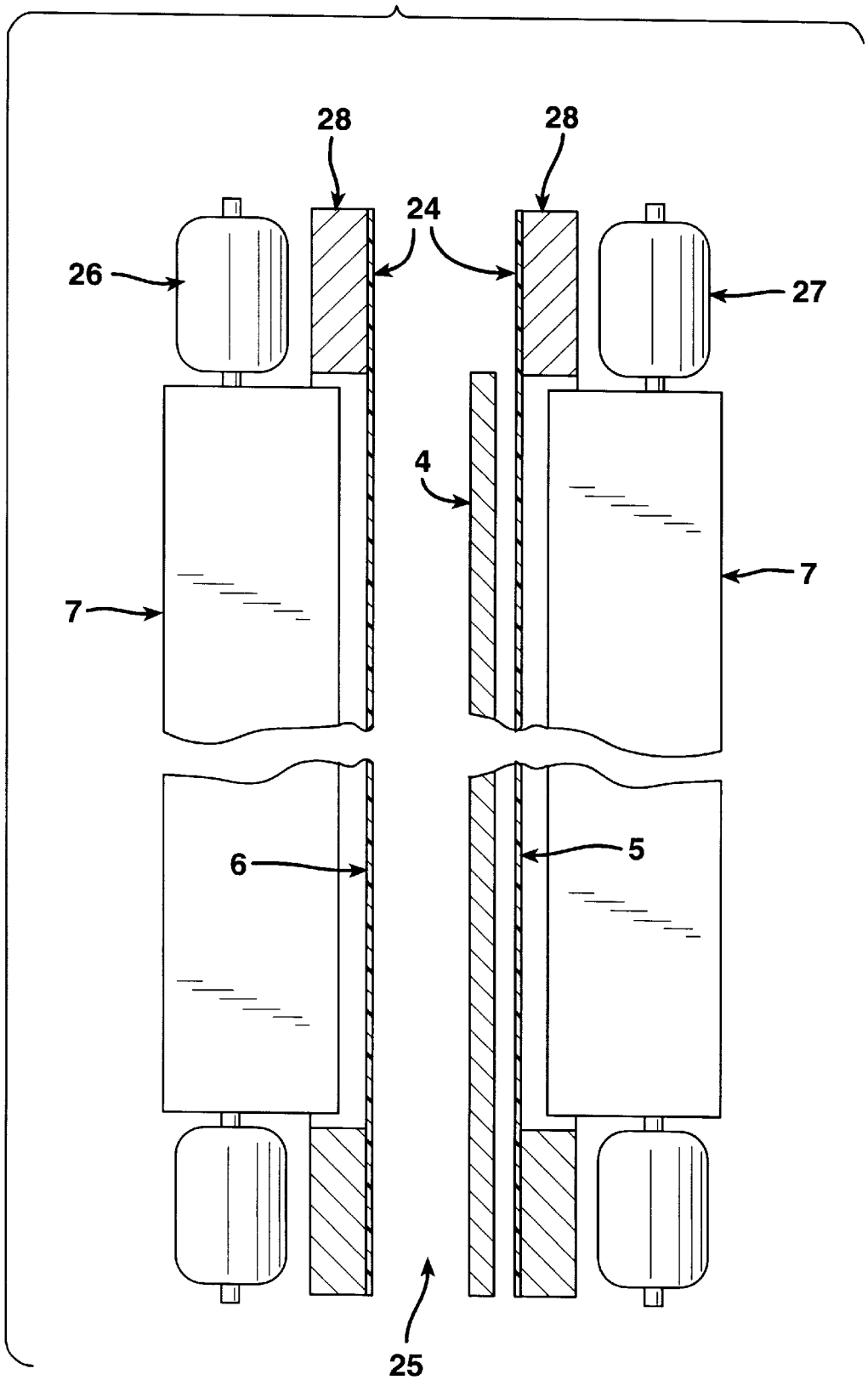
FIG. 5 shows a cross-section of the belt as indicated by the line labeled 5 on FIG. 4.

FIG. 5 shows a cross-section of the belt as indicated by the line labeled 6 on FIG. 4. This view more clearly shows the platens (7) pressing against the support belt (5) and "gel-side" belt (6). The view more clearly illustrates the two sets of opposable compression rollers (26) & (27) which, in one embodiment are laterally affixed to said platens, but which could be affixed to a frame or other support, and where these two sets of opposable compression rollers apply pressure to the continuously mating surfaces (24) on the lateral edges of both belts (5 & 6). The view also shows the space for the gel (25) and the gel backing (4) between both belts and the corded neoprene or other stiff lateral edge support on the belts (28).

The moving gel and support form the "downstream" end of the cavity as the gel polymerizes. The "upstream" end of the casting cavity is defined here as the end in which the reaction solution is introduced through the nozzles of the multi-chamber reservoir cylinder block. The "downstream" side of this cavity is defined here as the side formed by the solidifying gel as it hardens in the moving mold space. The length of this cavity is sufficient to provide enough time for the reaction mixture to solidify within the mold space at the particular speed that the belts are moving. A faster belt speed would correspond to a faster gel production rate and ordinarily a longer mold space, although one could contemplate increasing the rate of gel formation by increasing the gel reaction kinetics while the mold space remains constant. Both the support belt and "gel-side" belt are fitted such that they operate at constant speed as they move downstream during the polymerization process.

Figure 6:
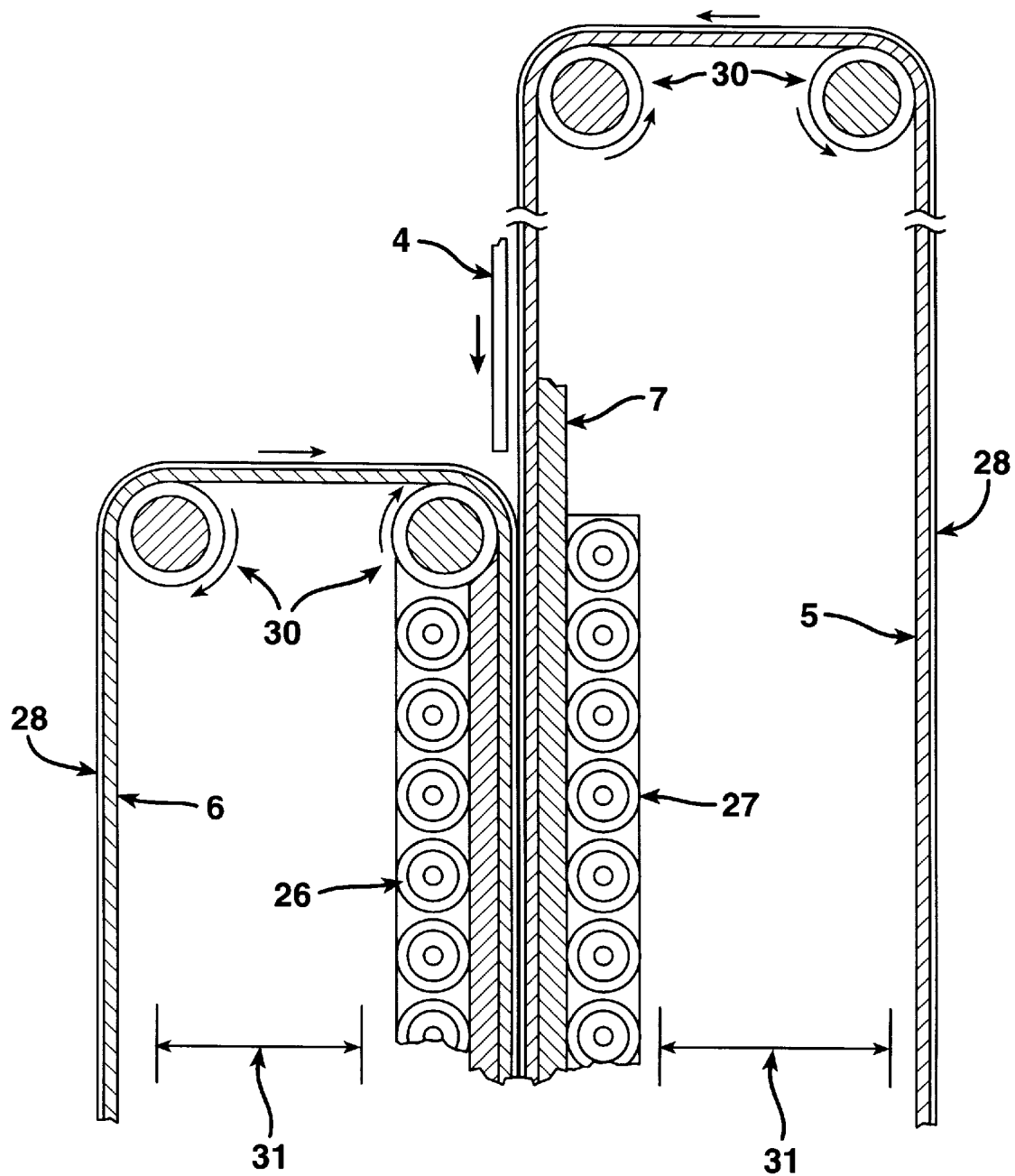
FIG. 6 shows the two large drive wheels which each individually drive a single belt in FIG. 4 are replaced by two smaller sets of drive wheels.

In FIG. 6 a preferred embodiment of the apparatus is shown. There, the two large drive wheels which each individually drive a single belt in FIG. 4 are replaced by two smaller sets of drive wheels (30). This allows a larger space (31) in the apparatus between driving and returning sections of belt. The larger space can more easily accommodate the platens, UV illuminator and compression rollers than single wheel drive belts. Other than the drive wheels previously mentioned, the other components of the apparatus are identical to those identified in FIG. 4.

A venting mechanism is also described which displaces entrained air in the molding space. Air or other fluids can be entrained in certain applications where the gel is to molded into a discontinuous support frame containing holes. The present invention provides a means of collecting any entrained air displaced by the reaction mixture as it flows out of holes present in the support backing (or also called a mask) on the back side of the belts (the side away from the side where the reaction mixture is introduced). A small chamber is provided which is filled with reaction mixture at a pressure that is just slightly below the pressure in the main cavity where the air bubbles can be removed as they float up into an air bell means at the top of the cavity. This air bell means has a release valve that can vent the air as it builds up while maintaining constant pressure. The accumulated gas vapor in bell is then periodically released to the outside air.

Figure 7:
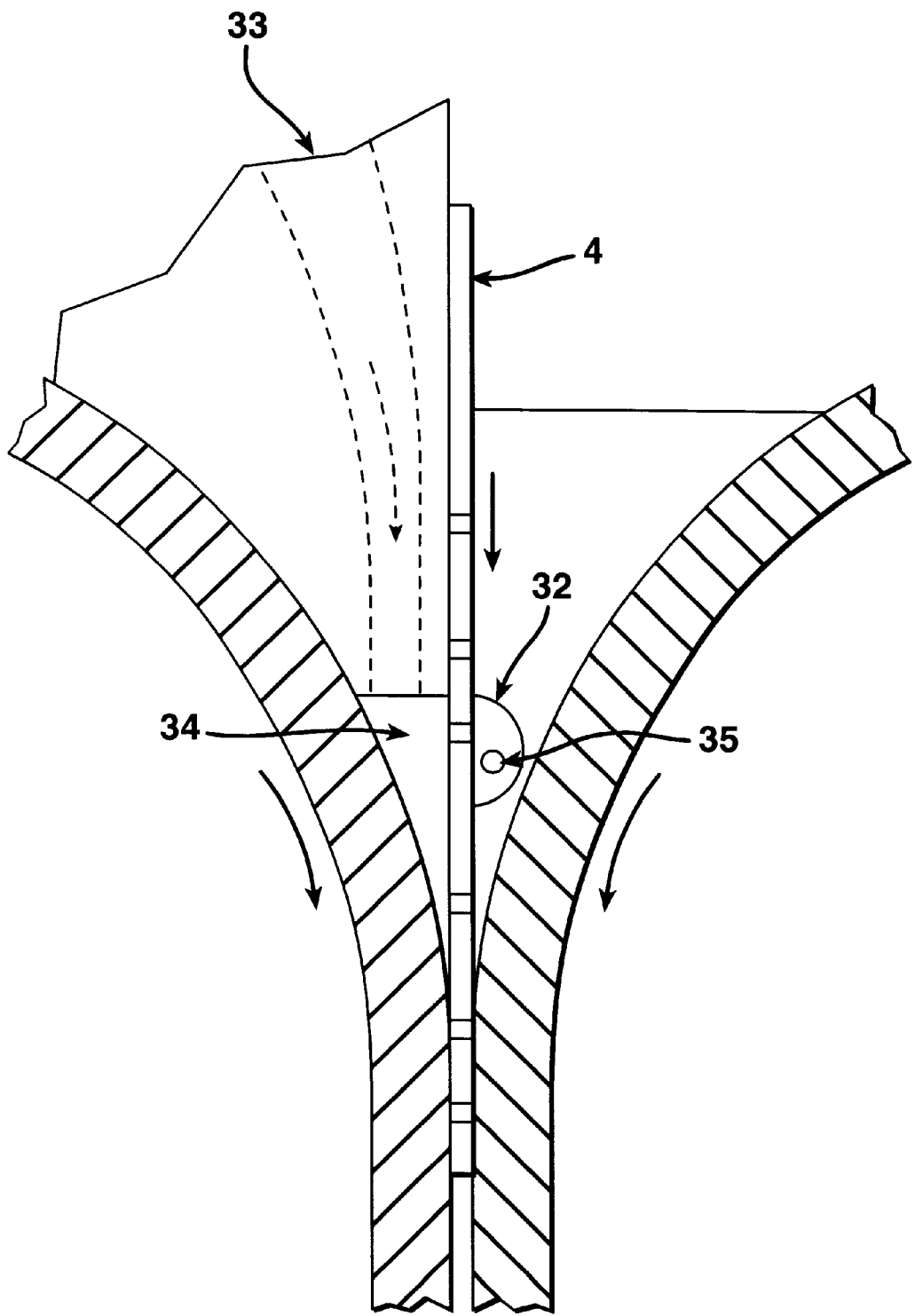
FIG. 7 shows in detail the means of removing air or any other unwanted vapor that may be entrained in the molding space at the upstream end.

FIG. 7 shows in detail the means of removing air or any other unwanted vapor that may be entrained in the molding space at the upstream end. Typically, this entrained air is from empty spaces in a support cassette or in the gel backing where it is desired to cast gel into these spaces. In an alternate embodiment these empty spaces are in a regular pattern and the mold is designed with a means of temporarily plugging the spaces and removing the plugs during the gel filling process. In yet another embodiment, where the empty spaces are irregular such as when a mask is cut to match the pattern of an image, and these cut holes are to be filled with gel. An air collector chamber (32) is included on the support belt side of the mask or backing or cassette (4). The support belt side is defined as the side of the belt carrying the backing or cassette opposite from the side the gel is applied to. The reaction mixture (33) enters the mold space cavity (34) on the "front side" of the mask or cassette. This allows the reaction mixture to displace the air from the empty spaces or holes in the mask or cassette into the air collector chamber on the "rear" side. Air entering this chamber (35) will rise to the surface of the reaction mixture and collect in the top of the chamber (as seen in FIG. 8) (36).

Figure 8:
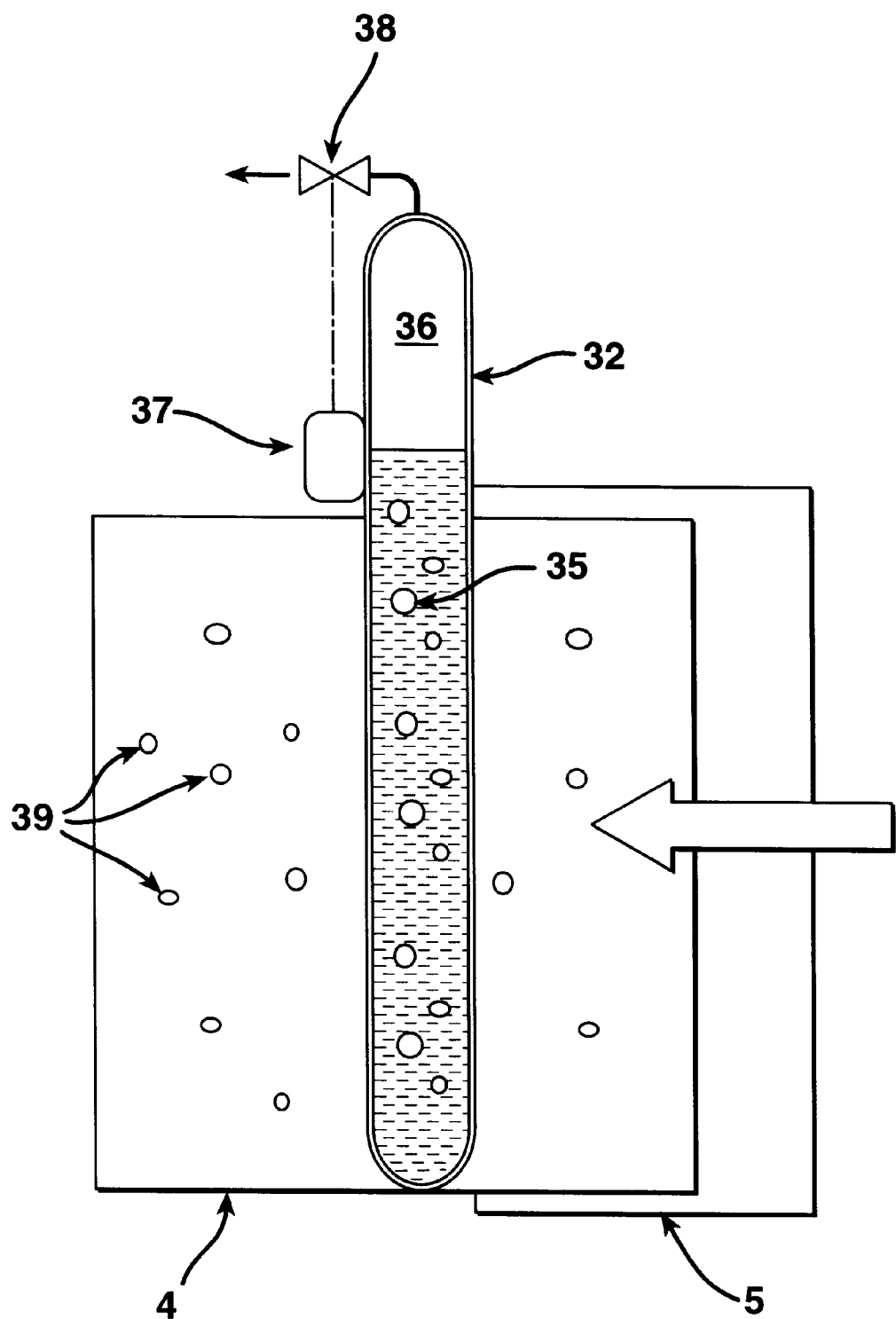
FIG. 8 shows the air collection chamber itself.

FIG. 8 shows the air collection chamber itself. The chamber has about the same pressure as the main mold cavity. As air builds up in the top of the chamber (36), a level detector means and controller (37) such as a conductivity switch that indicates when the level of the liquid, which is conductive, falls to a certain level indicating a build-up of air or other vapors. This means of level detection is located adjacent to the chamber, and maintains the air/liquid interface at a predetermined level by releasing air out the top of the collector chamber through a relief valve (38). In a preferred embodiment, only a small gel space is to be filled in these empty spaces (39) in the mask or cassette. In order to estimate the required flow rate in this case where the volume is small or undetermined, the amount of air released is equal to the amount of gel introduced. The overall flow rate of the reaction mixture is adjusted to match the average rate of air release, and in the preferred embodiment, is designed with an adjustable "dead-band" or hysteresis in the level of controller response to filter out short term variation in flow rate. One example of this type of control uses a delay timing in the signal to increase or decrease the flow rate of the pump. The level indicator must remain on for a predetermined time before the pump responds and the flow rate is changed.

As the reaction mixture enters the mold space a controlled means of initiating the free radical polymerization process is needed. Furthermore, chemical free radical initiators and catalysts require thorough mixing into the reaction mixture just prior to entering the mold space in order to prevent premature polymerization. In a preferred embodiment ultraviolet free radical generation is used to initiate the polyacrylamide polymerization reaction. This occurs through illumination within the molding space of a gel reaction mixture that contains a free radical photoinitiator such as riboflavin or benzoin, via a UV transparent window in the side of the mold cavity. For UV induced free radical initiation, one face of the mold cavity and belt, i.e., the front side, is provided with UV transparent materials at the wavelength for free radical initiation. An ultraviolet light source is also provided with a shutter means to allow the UV light to be dampened so as to control the reaction rate in the reaction mixture both spatially as well as temporally as the gels move down the cavity. In a preferred embodiment, the shutter allows the light to be dampened in both the vertical and horizontal directions.

Figure 9:
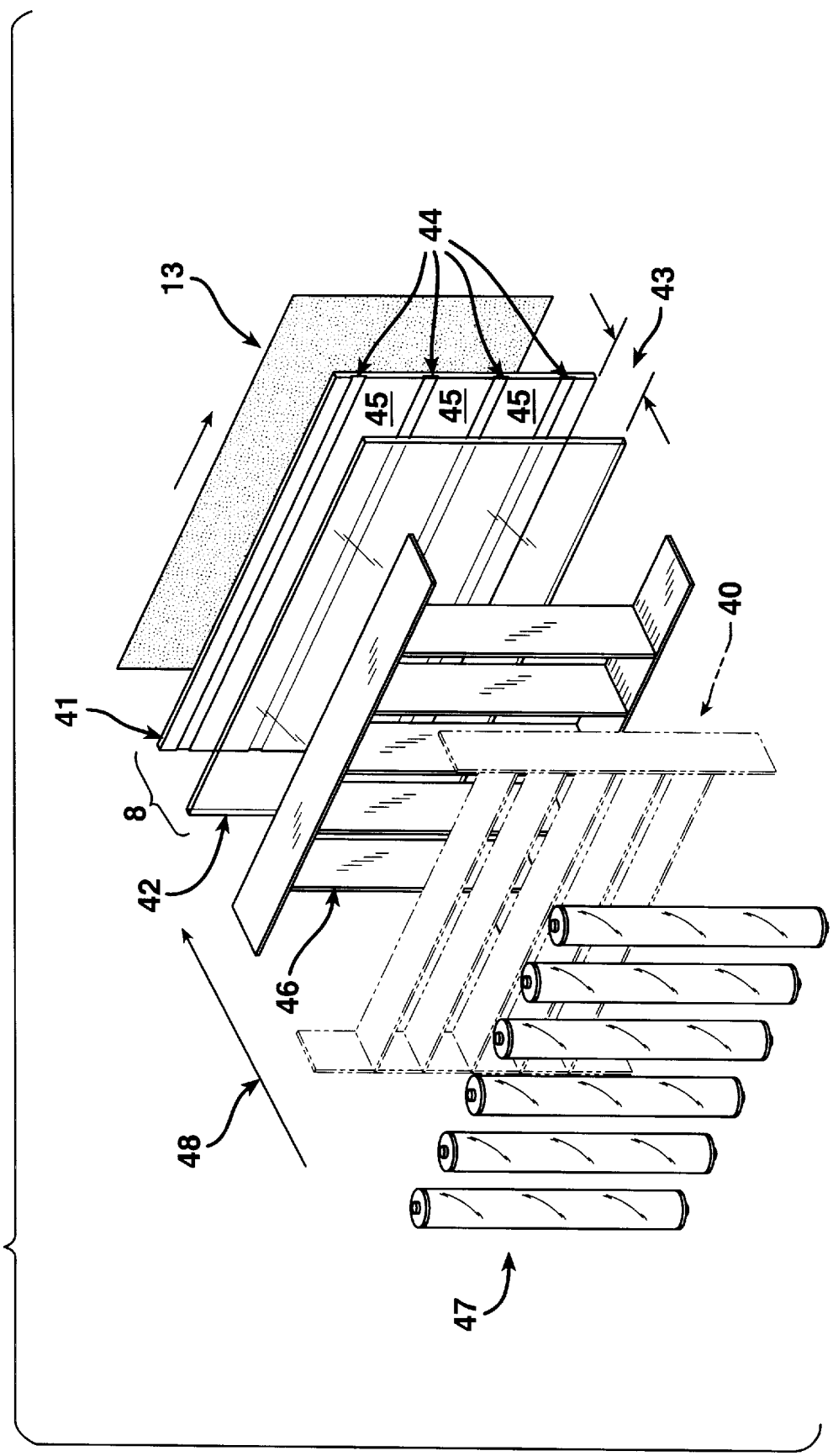
FIG. 9 illustrates the apparatus and method for photoinduced initiation of polymerization with use of a UV transparent window.

In FIG. 9 a UV transparent window (8) provides a means of initiating the free radical polymerization reaction in the reaction mixture by the irradiation of the reaction mixture (13) (held inside the UV transparent belt (6) and (5) with UV light after it has traveled into the molding space. This is the preferred embodiment of initiation of polymerization in the invention compared to chemically initiated polymerization because it has a less complicated delivery system and is potentially more accurate in controlling the polymerization of the gel. By use of a damping means such as a series of shutters (40), the level of UV illumination is varied in both the vertical dimension, corresponding to a possible compositional gradient, and in the horizontal direction, corresponding to polymerization time. A combined UV window and temperature control platen is composed of an ultraviolet transparent double window constructed of a laminate material (41) & (42) that has a minimum of absorption of light in the range of 300–450 nm, which corresponds to the range required to initiate free radical production in the reaction mixture. This window additionally must rigidly retain the "gel-side" belt. In a preferred embodiment the window also contributes to controlling the reaction temperature in the manifold space in a constant or gradient manner by being connectively attached to a heating or cooling means as described infra. To meet these requirements the window is comprised of two thicknesses of UV transparent material (41) & (42) that forms a laminar heating or cooling space (43) between them. In a preferred embodiment the window is comprised of glass. This laminar space is divided with UV transparent horizontal spacers (44) to form a series of channels (45) that allow for the variable control of temperature vertically by supplying a coolant gas or liquid such as water or air for example, with a different temperature to preferably each channel. Preferably the coolant or heating media is water. The UV window is supported rigidly against deflection, without substantially blocking the window from the UV light source, through a series of thin sheer web supports (46) in the vertical direction. These web supports are closely spaced as required so as to prevent appreciable deflection of the molding space under the hydrostatic pressure conditions of the polymerization reaction. In the preferred embodiment, this would be a spacing about ten to twenty times the thickness of the transparent UV window and depends on the modulus or elasticity of the window material. Appreciable deflection is defined more than 1–2% variation in the mold space thickness. A bank of UV sources (47) in the long wavelength range of about 300–450 nm are provided and are arranged to illuminate the window uniformly. The arrow (48) shows the direction of UV light propagation. In a preferred embodiment, a set of optional shutters or masks (40) are provided for variation in the intensity of the illumination either vertically or horizontally.

Figure 10:
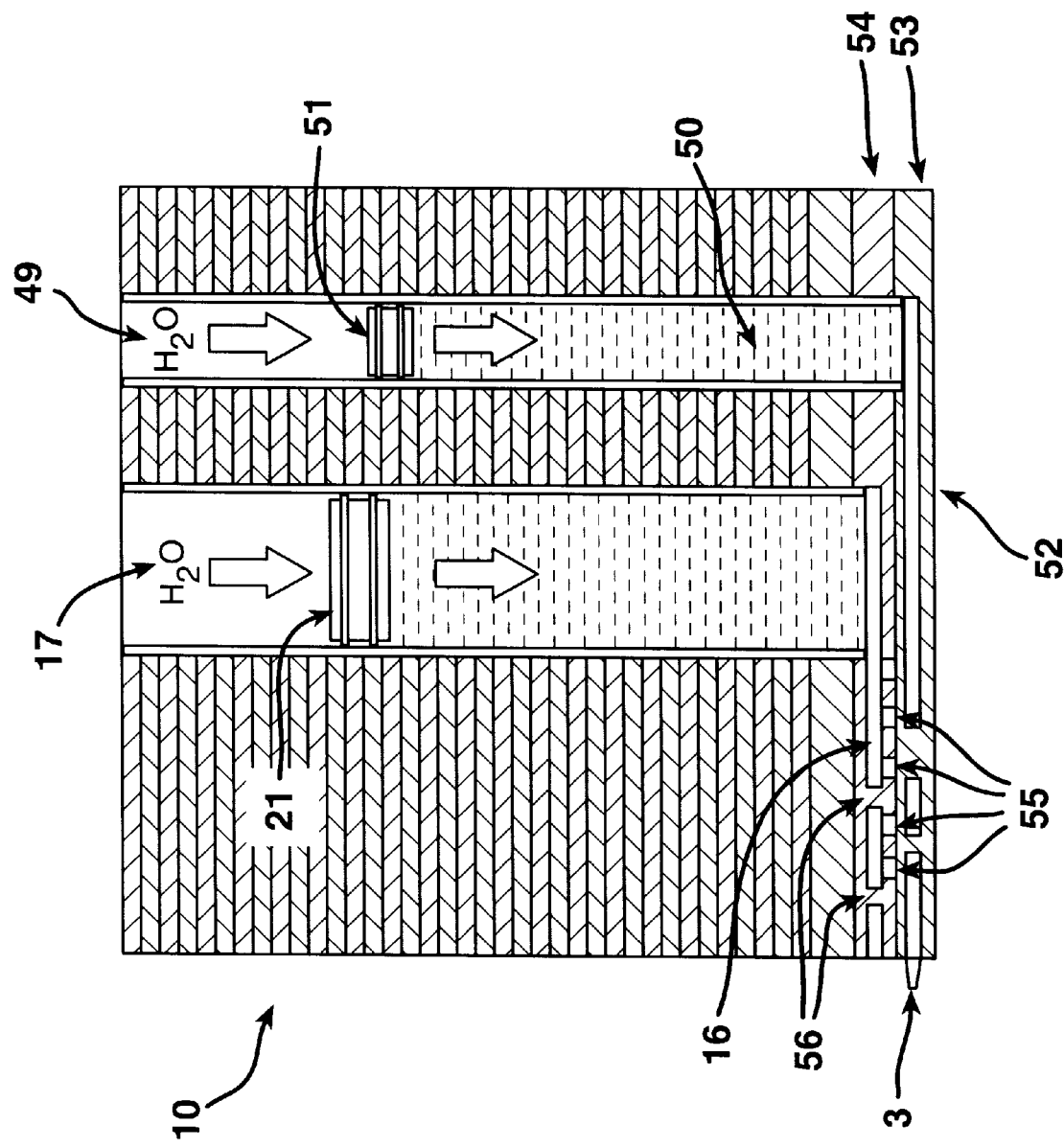
FIG. 10 illustrates one embodiment of an apparatus and method for chemical initiation of polymerization option 2-two part reaction formulations.

The apparatus shown in FIG. 10 provides for an alternate embodiment, in which chemical initiation of polymerization, by chemical generation of free radicals (such as peroxides and persulfates), of the gel is used. For chemical initiation, a second set of cylinders in the multichamber cylinder block is required for each gel formulation that can segregate the monomer from the initiators in two compartments. All other components of the reaction mix can be divided between these two compartments. As the solution in each compartment is delivered to the horizontal delivery channel it follows a path to mix with the solution in the other compartment prior to entering the mold space. The flow rate and the path length are comprised to minimize the time it takes for the initiated reaction mix to reach the mold space. Typically this should be less than 3–5 minutes. The two cylinders for each formulation can have the same cross-sectional area or different cross-sectional areas as required to achieve the necessary formulation parameters but must have the same hydraulic pressure. The volume ratio of the two reaction mixtures must match the cross sectional area ratio of the two cylinders of each formulation pair. Additional control over polymerization conditions by varying the concentration of initiators from one incremental formulation to the other provides the means of graded control of the reaction rate along the vertical (gradient) dimension of the polymerizing gel.

The apparatus shown in FIG. 10 is used for those embodiments where free radical polymerization reactions are initiated by chemical generation of free radicals (such as peroxides and persulfates). It should be noted, however, that the secondary, usually smaller, reservoir that feeds into a particular nozzle can be used to provide a constant pressure expansion chamber for each formulation in order to accommodate intermittent changes in the rate of delivery of the reaction mix as well. In this embodiment, the secondary reservoir is used as a constant pressure expansion chamber to accommodate flow fluctuations, and the fluid or pressure medium in the inlet half of the cylinder, above the piston, is not a liquid (such as water) but a gas (such as air). The source of this air is a connection to a pressure tank which is pressurized to supply the necessary fluid pressure at the nozzles. This accommodation of flow variation is of particular use in those applications where a pressure and flow buffer are needed such as when the reaction mixture is to be polymerized into a strip or hole in a support cassette or holder instead of the preferred embodiment, where a connected laminar gel completely fills the mold cavity. In those applications where a smaller cylinder within a larger cylinder is not available to provide a pressure and flow buffer, such as when it is being used to mix components for chemical initiation of polymerization, a secondary reservoir (49) is fitted with a glass column (50), O-ring seals and a piston (51) or a flexible membrane that divides the chamber into two compartments to provide an expandable volume lower compartment, in essentially the same manner as the primary reservoir. The secondary reservoir terminates the horizontal delivery channel of the same layer as the primary reservoir between the primary reservoir and the nozzle.

A means of mixing the contents of a primary reservoir (17) and a secondary reservoir (49) is provided by an interconnection of the horizontal channels (16) and (52) in the two adjacent layers (53) and (54). Mixing is accomplished using a series of vertical slots or holes (55) and barriers (56) formed in the layers. The movement of the fluid from the reservoirs through the tight series of channels and spaces creates vortices and currents that mix the two fluids. The formulation of the reaction solution in the two reservoirs is such that one or more components of initiation are segregated from the monomer until mixed in the channels. The combined and mixed reaction solution with the polymerization reaction initiated flows to the nozzle (3) in the usual manner and into the mold cavity. The top of the secondary reservoir (49) terminates in the same layer as the primary reservoir (17) and is connected to the same drive fluid and pressure as the primary reservoir.

Figure 11:
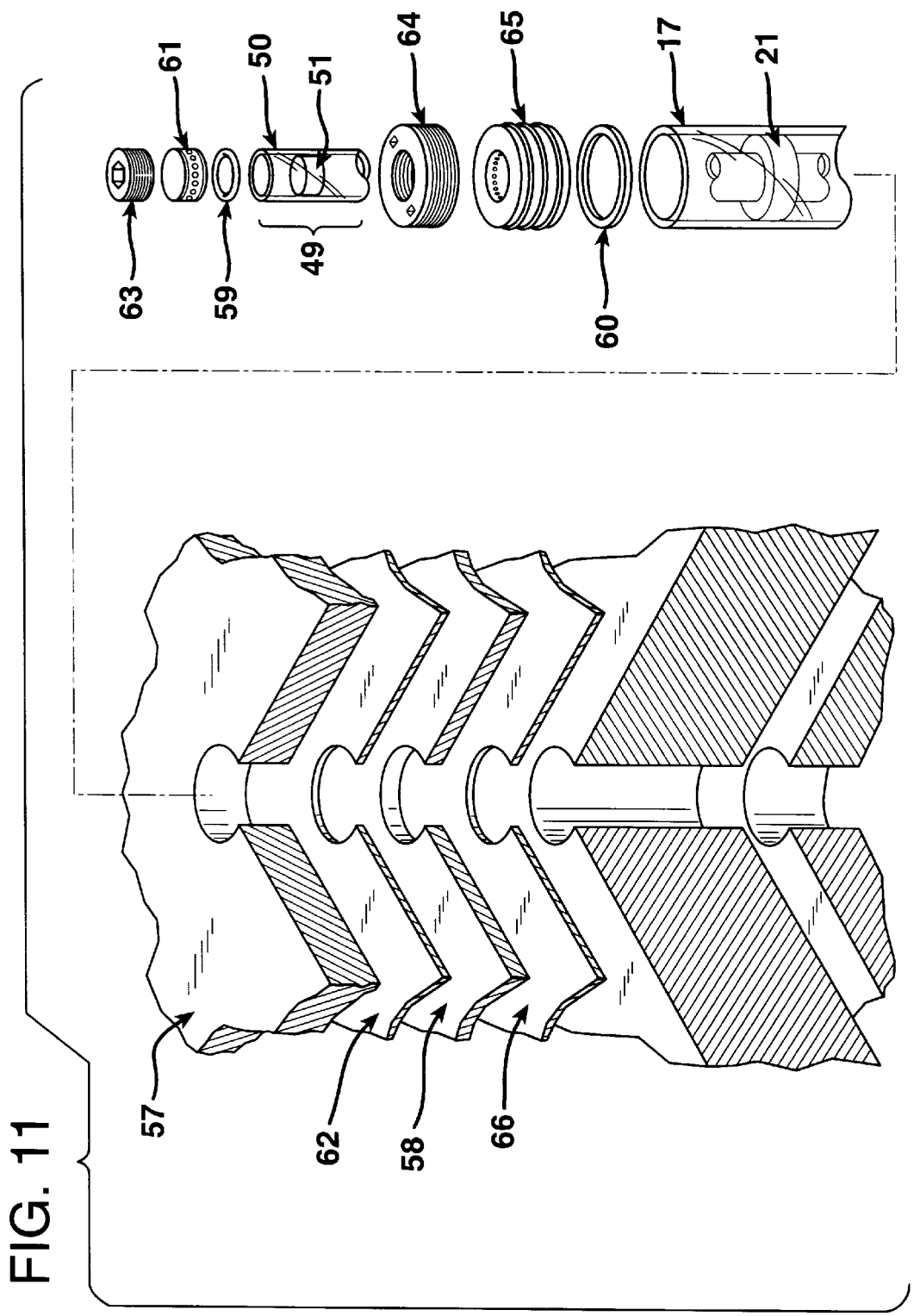
FIG. 11 illustrates the top-half of a preferred embodiment of an apparatus and method for chemical initiation of polymerization option 2-two part reaction formulations.

An alternate embodiment, which is a preferred embodiment for those embodiments where free radical polymerization reactions are initiated by chemical generation of free radicals is illustrated in FIG. 11. The apparatus shown in FIG. 11 solves the problem of handling two-part reaction mixtures wherein the ratio of the volumes between the two reservoirs for each formulation can be varied by almost any amount by choosing a secondary reservoir diameter that is less than about ⅔ of the diameter of the primary reservoir. The secondary reservoir in this embodiment is positioned concentrically within the primary reservoir. The two reservoir glass columns (17) and (49) both having top (drive fluid end) ends which terminate in adjacent multi-layer cylinder block layers (57) and (58), and both having bottom (reaction mixture end) ends which terminate in the same cylinder block layer (59, FIG. 12 and FIGS. 14 ). The two reservoir glass columns (17) and (49) both have nylon rings with square cross-sections which are disposed on top of said reservoir glass columns. The nylon ring which fits on top of the secondary reservoir column is called the inner compression O-ring seal (59), and The nylon ring which fits on top of the primary reservoir column is called the outer compression O-ring seal (60). An inner compression ferrule seal (61) fits snugly on top of the inner compression O-ring seal and allows secondary reservoir drive fluid (62) from its laminar layer, into the upper compartment of the secondary reservoir. This inner compression ferrule seal is illustrated in more detail in FIG. 13. An inner compression screw cap (63) screws into the inner threads of an outer compression screw cap (64) and thus applies pressure onto the inner compression ferrule seal.

Similar to the secondary reservoir, an outer compression ferrule seal (65) (also shown in more detail in FIG. 13) fits snugly on top of the outer compression O-ring seal and allows primary reservoir drive fluid from its laminar layer (66), into the upper compartment of the primary reservoir. An outer compression screw cap (64) thus applies pressure onto both the inner compression ferrule seal as well as the outer compression ferrule seal when the secondary reservoir is fit within the primary reservoir as shown in this exploded view in FIG. 11.

Figure 12:
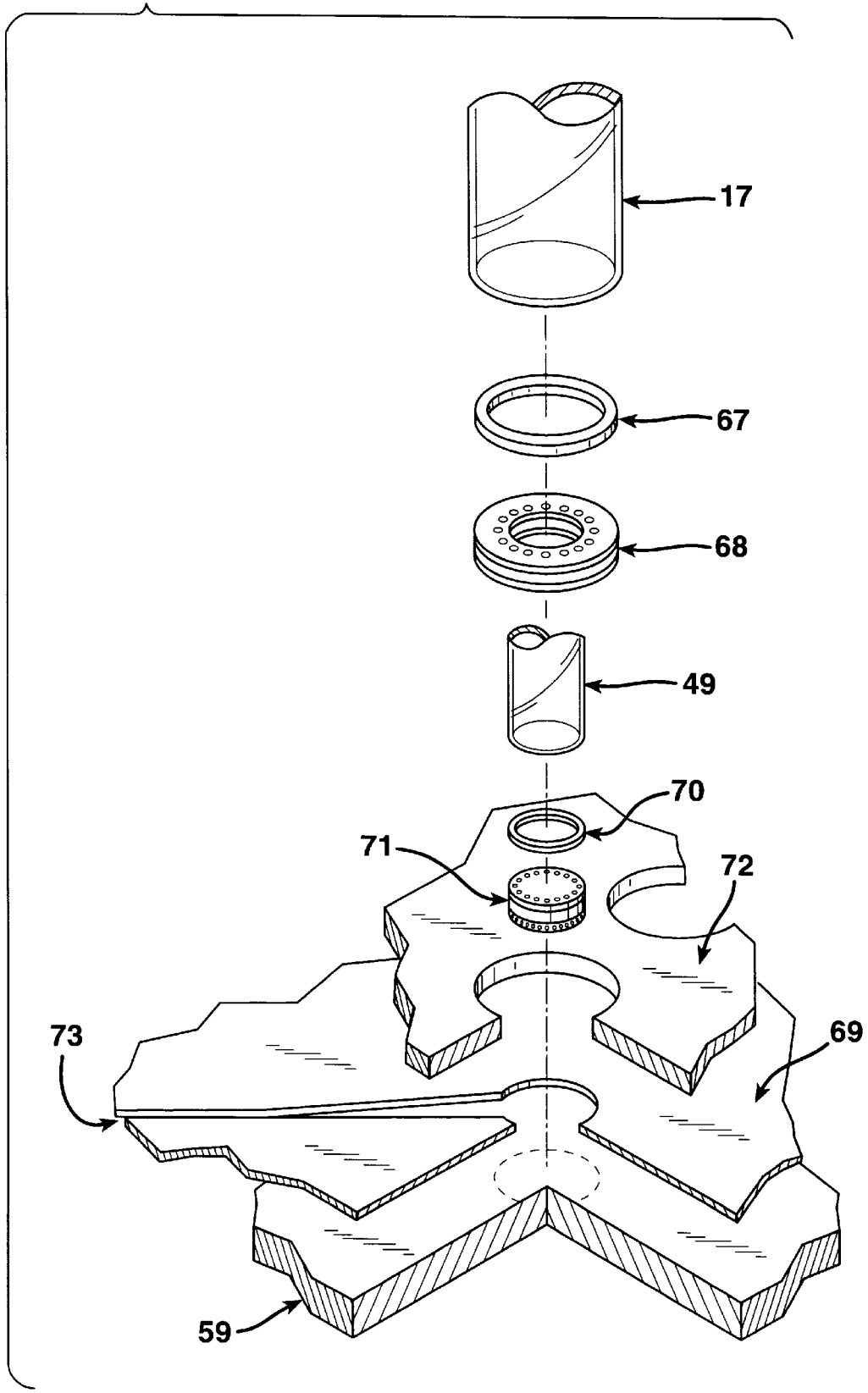
FIG. 12 illustrates the bottom-half of a preferred embodiment of an apparatus and method for chemical initiation of polymerization option 2-two part reaction formulations.

FIG. 12 shows the bottom half of the preferred cylinder block arrangement. Again, the primary reservoir travels through the laminated layers and through a elastomeric layer (69) and terminates in a lower outer compression O-ring seal (67) which seals against a three layer orifice ring (68) having a plurality of vertical holes drilled circumferentially about the center and which has disposed in its center the secondary reservoir column and which then is seated on the base layer (59). The secondary reservoir column similarly terminates in a lower inner compression O-ring seal (70) which seals against a three layer orifice plate having elbow type channels (71) which is positioned through the elastomeric layer and within the three layer orifice ring and which is also seated onto the base layer. The cylinder block laminations (72) and (59) are separated by an elastomeric gasket (69) having disposed within each reservoir, horizontal channels (72) which connect the reservoir contents to its individual nozzle (73).

Figure 13:
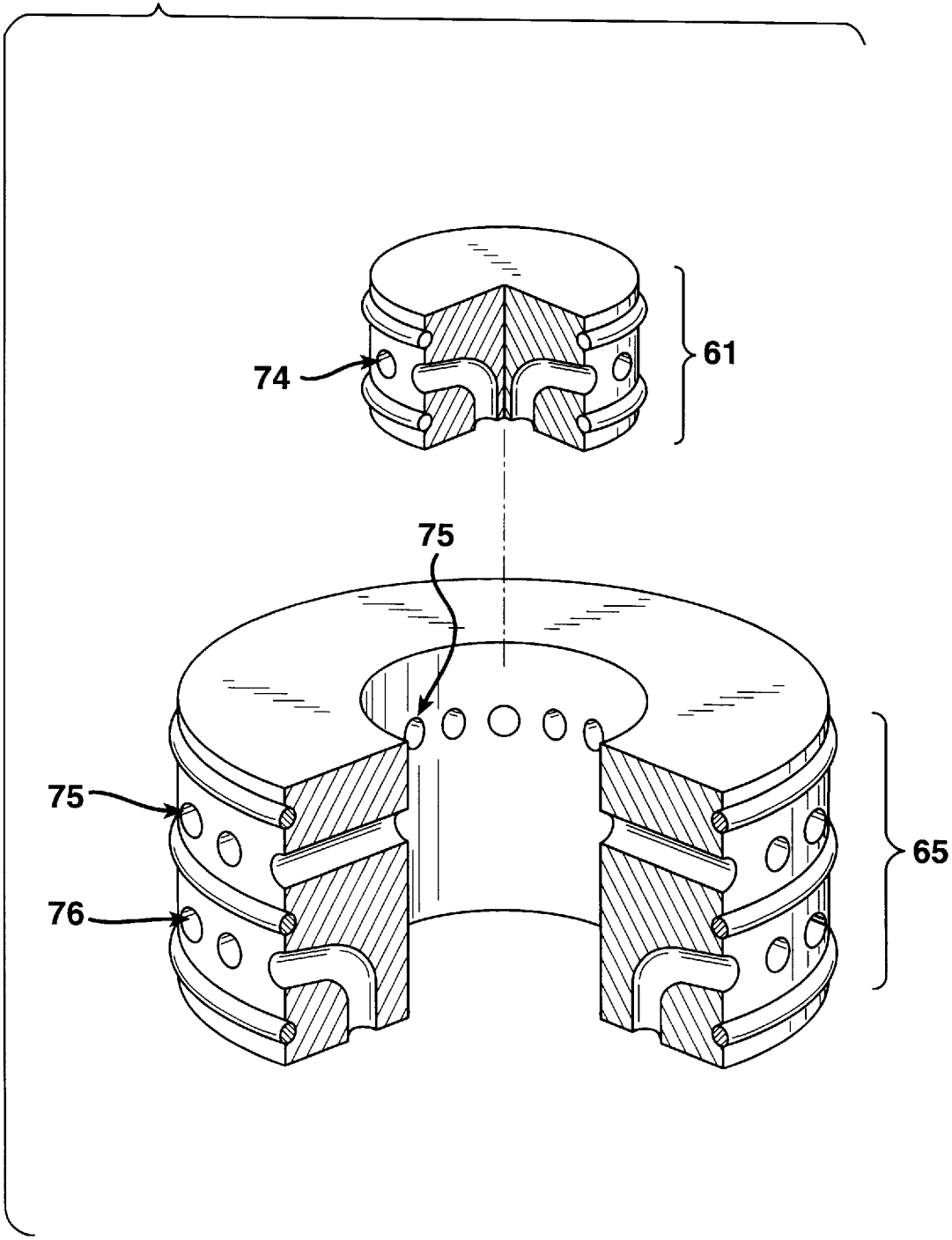
FIG. 13 shows detailed cutaway views of both the inner and outer compression ferrule seals.

FIG. 13 illustrates the details of inner (61) and outer (65) compression ferrule seals in each reservoir column. Said inner compression ferrule seal fits within the center of said outer compression ferrule seal such that the secondary drive fluid inlet holes (74) of the inner compression ferrule seal communicate with the secondary drive fluid inlet holes (75) of the outer compression ferrule seal and allow drive fluid to enter the secondary reservoir. The outer compression ferrule seal also has a second set of concentric holes or channels called the primary drive fluid inlet holes (76), which are adjacent and below the secondary drive fluid inlet holes. The primary drive fluid inlet holes allow drive fluid to enter the primary reservoir.

Figure 14:
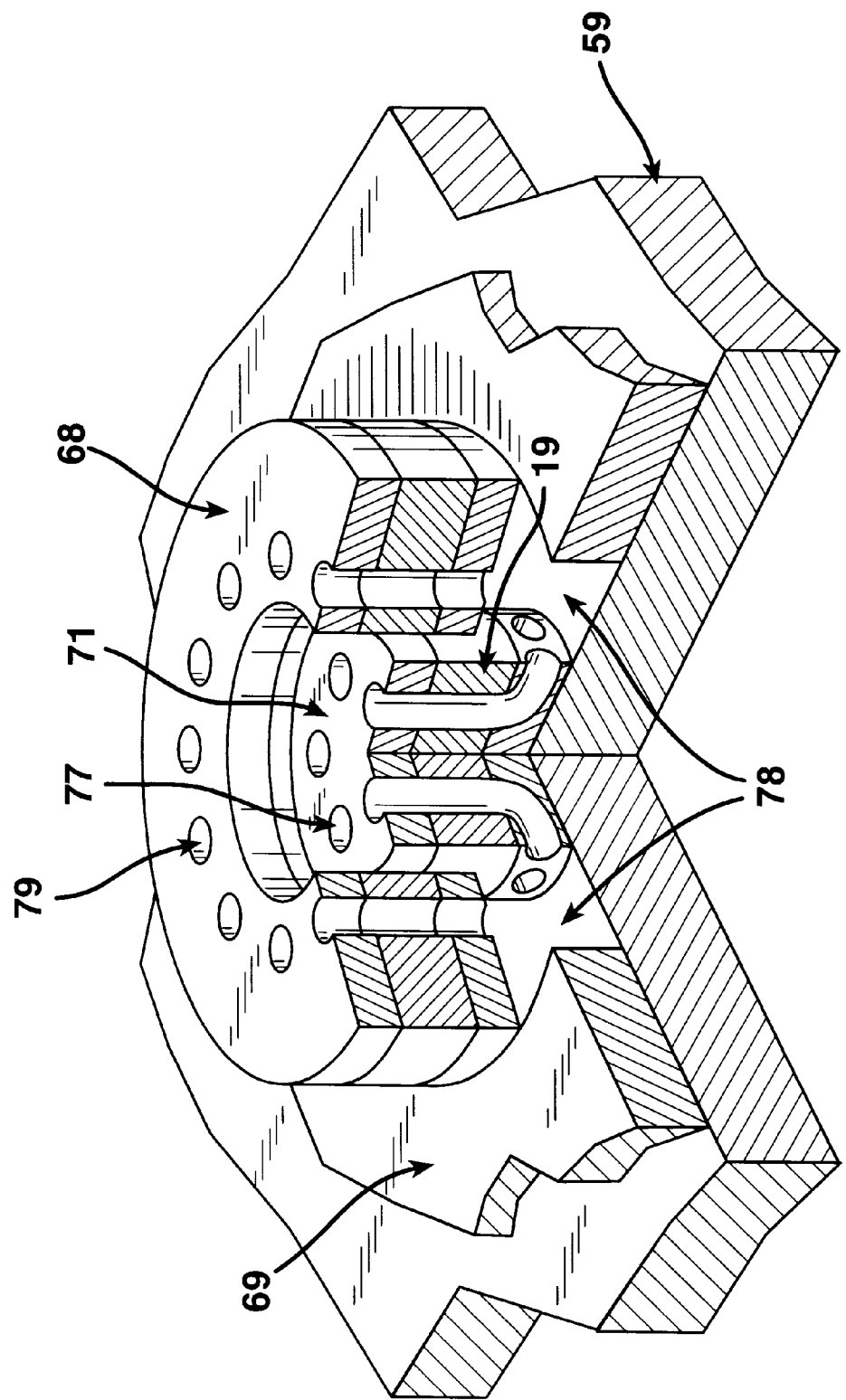
FIG. 14 shows detailed cutaway views of both the 3-layer orifice ring and 3-layer orifice plate.
Figure 15:
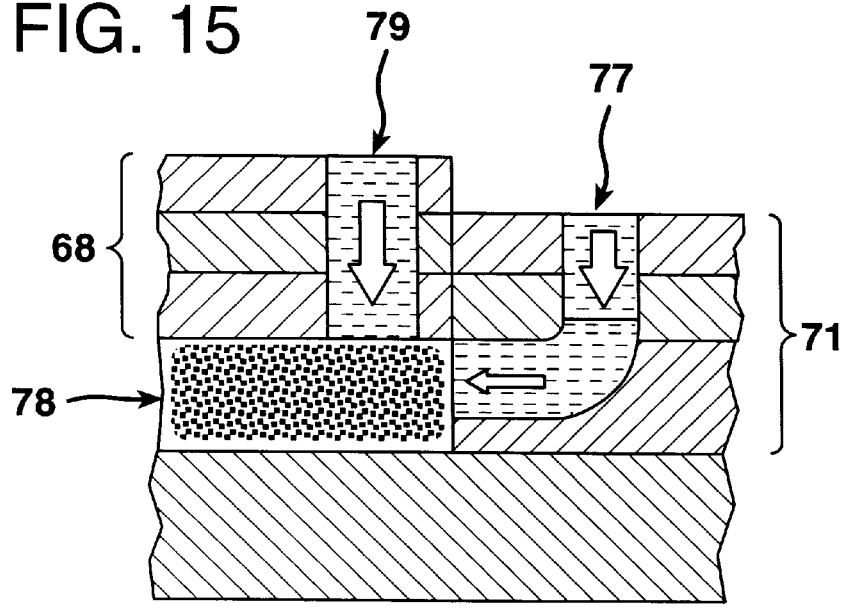
FIG. 15 shows a detailed cross-section of FIG. 14.
Figure 16:
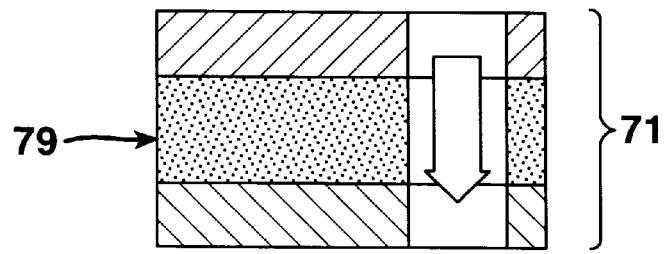
FIG. 16 shows a detailed cross-section of the 3-layer orifice plate in a non-compressed state.
Figure 17:
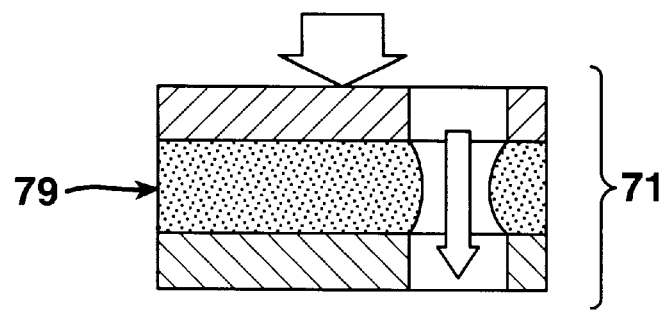
FIG. 17 shows a detailed cross-section of the 3-layer orifice plate in a compressed state.

FIG. 14 illustrates the details of the three layer orifice ring (68) and the three layer orifice plate (71) as they are disposed between the elastomeric layer (69) and seated on the terminal layer (59). In a more preferred embodiment, the orifice plates are three-layer orifice plates which are constructed out of a lamination of two outer layers of a high rigidity material. This rigid material could be steel or other metal alloy but is not necessarily limited to a metallic composition. Said more preferred embodiment also has an elastomeric inner layer that is compressible and is illustrated in detail in FIGS. 16 and 17. The three layer orifice plate terminates contains a plurality of elbow-like channels which allow reaction mixture from the secondary reservoir to enter an annular mixing space (78). The three layer orifice ring has a plurality of vertical channels (79) which terminate in the layer above the elbow-like channels of the three layer orifice plate, and communicate with said annular mixing space. This annular mixing space allows the primary and secondary reaction mixtures to mix together in a controlled proportion prior to emptying into said nozzle in a controlled manner. A cross-section of FIG. 14 is shown in FIG. 15.

The amount of secondary reservoir mixture (which could be a chemical initiator or additional reaction mixture or some other necessary compound or composition) is controlled by the amount of pressure applied to the secondary reservoir column through tightening or loosening the screw cap (63). When a vertically oriented compressive force is applied to the glass columns at their tops, they transfer the force to the three-layer orifice plates. Compression of the three-layer orifice plate causes the elastomeric inner layer (79) to bulge out circumferentially and partially occlude the orifice openings. This occlusion constricts the flow and causes increased back pressure in the occluded flow streams relative to the unoccluded streams. Said vertically oriented compressive force is generated by the screw cap (63).

Typically, the variation in flow rate generated by this means of calibration or flow control from compartment to compartment is only that which is required to maintain uniform flow rates to each nozzle such that the delivered volume from any one reservoir does not deviate by more than 0.5% in the integral over the total production run relative to the mean delivered volume from each reservoir. The required variation in flow rate is in the range of no more than 5% of the total flow for each reservoir and typically much less. The transversing channels at the inlet end in the screw caps are geometrically configured so as to provide an uninterrupted connection to the drive fluid as the screw cap is rotated.

This preferred embodiment for the fine tuning and calibration of flow rates between reservoirs can also be used as a preferred embodiment for those applications wherein there is a single component reaction mix to be delivered to the mold space but it is desired to calibrate and fine tune the flow rate between reservoirs. In this embodiment, where a smaller cylinder is not provided, the orifice plate (71) is eliminated, as is the inner compression screw cap (63) and the orifice ring (68) is configured to be a solid plate without a hole in the middle. The three layered construction or the orifice component is provided with transversing channels as before. Compression force is applied through the walls of the single glass or plastic cylinder in each cavity to the orifice component to deform it and modify the flow rate by creating variable pressure drop across the transversing channels in the orifice component. This provides for the fine-tuning and control of flow rates from reservoir to reservoir. As before the required variation in flow rate is in the range of no more than 5% of the total flow from each reservoir and typically much less.

In a series of alternate embodiments, the platens may also provide temperature control and UV illumination, and are described in more detail in FIGS. 18 and FIG. 19. Both of these rigid platens (7) have a finely adjustable gap between them that must not be distorted more than 1–2% by pressure variations for the entire range of useful pressures (0–1 atmosphere above ambient pressure). The gap is created by careful positioning and alignment of the platens on their support structure (FIG. 19) (80) by adjustable screws (81), and the gap is varied by adjusting the position of the platens (7) with their mounting screws (having preferably thread pitches of less than 0.5 mm). Fine adjustment of the belt speed during casting can control the manifold pressure as the flow rate of the reaction mixture remains constant.

A means of controlling the reaction temperature in the mold during the exothermic polymerization is required and is shown in FIG. 18. In FIG. 18, the platen walls of the continuous casting apparatus, that support and provide dimensional stability to the belts, also contain a series of channels that allow for temperature control. Said temperature control is accomplished by a flow of water or air that is maintained at the temperature required to maintain the desired reaction temperature. A series of manually adjustable blending valves is provided that controls the temperature of small zones, both vertically and horizontally in the polymerization space of the continuous casting apparatus by mixing hot and cold supplies. These temperature zones are maintained throughout the processing of a batch of gels.

FIG. 18 shows an embodiment in which rigid platens may enclose and support the front and back continuous belts. In this embodiment, these platens perform multiple functions in the continuous casting apparatus. For example, in FIG. 1, the front platen (7) provides a means of illumination for initiation of polymerization in those applications that require it (as in UV induction of polymerization) and both platens provide lateral deflection resistance to the continuous casting mold space to maintain close tolerances on the thickness of the gel product. Third and fourth functions will be described here. Polymerization reactions are dependent on many parameters. Complex gradient polymerizations are heterogeneous in their polymerization rate due to differences in the concentration of the reactants in micro-environments within a gel and are particularly difficult to control. It is desirable to be able to control the temperature of a polymerization reaction as a function of time and vertical distance along the gradient. The present invention provides a unique temperature control in both dimensions. Front and back platens are provided in FIGS. 18 and FIG. 19 that have the necessary rigidity and/or UV transparency while providing for the control of reaction temperatures in the mold space. The temperature control may include both addition of heat to the gel reaction and the removal of exothermic heat from the reaction as well.

Each platen consists of two plates (FIG. 19) (82) and (83) constructed of rigid thermally conductive relatively low expansion materials from a list that contains aluminum, stainless steel, Pyrex glass, ceramics or other thermally conductive materials. For the non-UV transparent platens, stainless steel is preferred while for the UV transparent platens, Pyrex or other low expansion glass is preferred. These plates are arranged in layers in order to provide a heating/cooling manifold with horizontal channels (FIG. 18 (84) and FIG. 9 (45)) for the flow of coolant. A gasket or spacer (FIG. 8 (85) and FIG. 9 (44))) which may or may not be constructed of UV transparent materials between the two plates is provided to separate these channels. There is a hot (86) and cold (87) coolant supply manifold and provided to each platen and a single return line (88). In a preferred embodiment, one coolant supply manifold is located in each inward facing plate and the return manifold is located in each outward facing plate away from the belt. These channels run vertically throughout and along the ends of the platen with the supply manifolds on one end and the return manifold on the other in a direction of flow that is counter-current to the direction of the advancing gel. At the opening between each horizontal channel and each vertical supply manifold is a manually adjustable blending valve (89) (of a general type having two opposing valve washers on a stem that is disposed between the plates of said platens and perpendicular to said platen so that each washer can in turn seal against a valve seat at the inside surface of said plates at their opening) thereby varying the temperature of the coolant by blending variable amounts of hot and cold coolant.

Figure 20:
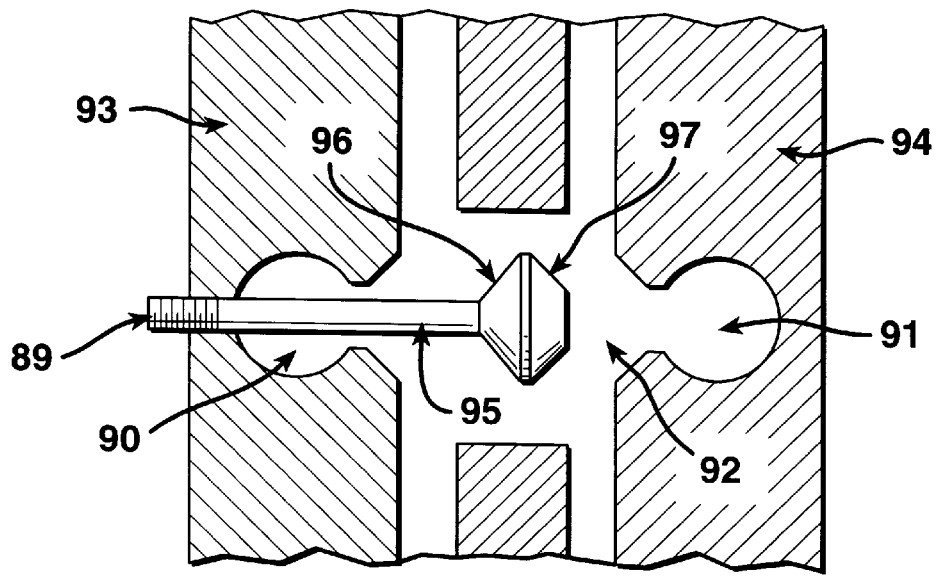
FIG. 20 shows a cross-sectional view of a temperature control platen manual valve assembly.
Figure 21:
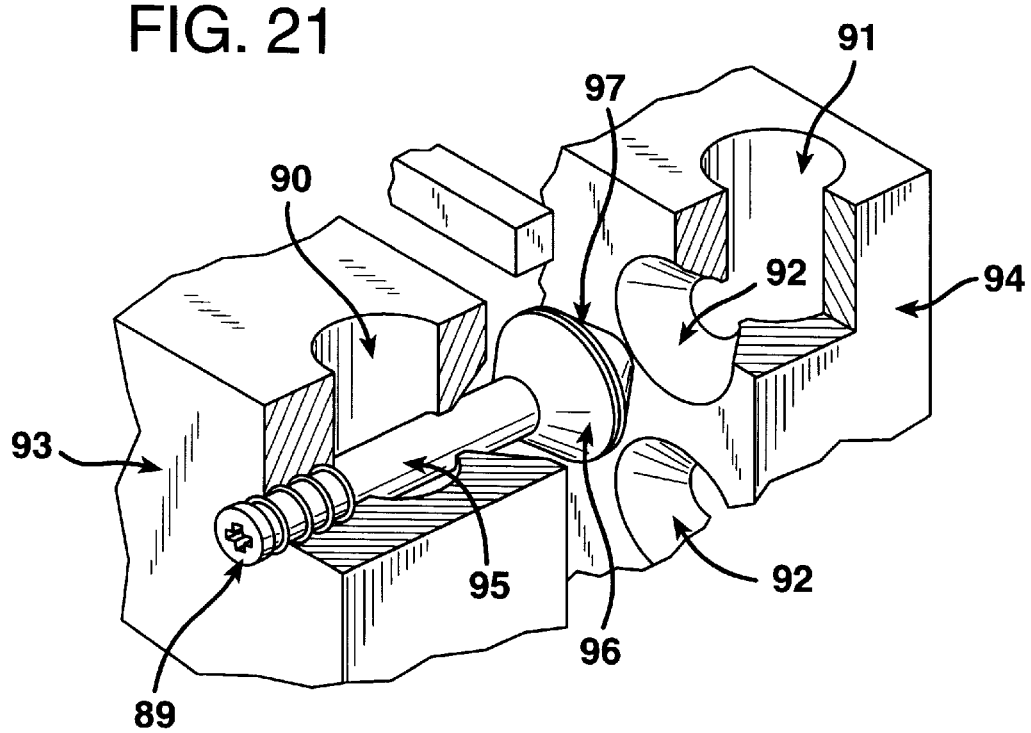
FIG. 21 shows a 3-dimensional view of a temperature control platen manual valve assembly.

A preferred embodiment of this temperature control apparatus is shown in detail in FIG. 20 (a cross-section) and FIG. 21 (3-dimensional view). The valve provides for the connection between the vertical manifold channels (90 & 91) and a horizontal channel to be comprised of a conical valve seats (92) machined into or attached to the outboard and belt side plates (93 & 94) containing the vertical manifolds where the manifolds connect with the horizontal channels. These conical valve seats are widest at the face of the plate that forms the horizontal channel. A valve stem (95) that contains two opposing valve washers (96 & 97) that are mounted on the valve stem in such a manner that each one is capable of seating against one of the valve seats (92). The valve stem is mounted perpendicular to the face of the platen such that the valve washers are on the horizontal channel side of the plates and the steam extends through the outboard plate (93) necessarily passing through the vertical manifold space. The geometry of the overall assembly is such that only one valve washer can be seated at a time and the valve stem is provided with a means of transverse motion in order to effect a variation in the relative amount of coolant flowing from each supply manifold.

For example, a provision for threading between the stem and the plate and a means of applying torque to the stem in order to rotate it and effect transverse motion thereby altering the relative space between each valve washer and its corresponding valve seat (92) is described. The valve stem is also provided with a means of sealing between the threaded section of the stem and the vertical manifold in order to prevent leakage of coolant at the stem protrusion through the plate. This embodiment provides an economical way of calibrating the large number of temperature control zones required along the full length of the continuous casting line. Once adjusted and calibrated these valves remain set for the duration of a production run.

The platens are held in place by support brackets (80) on each side. In a preferred embodiment, the platens are attached to these supports in at least 4 locations with finely adjustable screws (81) preferably having tread pitches of less than 0.5 mm that allow for alignment and adjustment of the gap between the front and back platens. The adjustment of the gap determines the thickness of the molding space under pressure. Each platen is provided with a means of connection on the ends to additional platens to provide the necessary length required for the gelation time of the run at a given belt speed.

A means of removing the completed gels from the molding space is provided. It is preferred that any mold flesh (excess gel) is removed at this point. By unsealing the front and back belts as they move over the exit rollers at the downstream end of the continuous casting line, the completed gels, which are connected to one another as a consequence of continuous casting, move into a means for cutting and stacking the produced gels on a continuous basis, providing a major advantage of the present invention over batch casting methods. The completed gels, cassettes or masks can be stacked into a magazine or other support for further processing, They can also be stacked into their running cassettes ready for immediate use.

The following examples will illustrate the optimization of the prototype apparatus:

EXAMPLE 1
DNA Fragment Analysis

The continuous casting process of the present invention, not only allows the optimization of local gel matrix conditions for high resolution and even spacing for each fragment length, but holds the promise of orders of magnitude improvement in the loading, running and imaging of DNA sequencing gels using a continuous belt from beginning to end, without set up or take down steps. This technology will be capable of virtually unattended operation from the point of casting and loading through data capture. Simply increasing the length of the continuous belt supporting the gel matrix in such a system can increase the speed of sequencing throughput.

The first step determines the limits of resolution and density of DNA fragment analysis possible within compositionally optimal complex gradient gel using state of the art image analysis techniques. This investigation measures mobility and resolution empirically but is guided by a theoretical description of DNA migration in the various migration regimes that apply to acrylamide gel electrophoresis.

In addition, the minimal thickness (and therefore maximal run speed) compatible with the continuous casting gel process and the constraints of available imaging sensitivity are determined. A thickness variation tolerance of less than 5% of the cast gel is the target.

EXAMPLE 2
Limits of Resolution

In this example, the goal is to determine the maximum information density that can be obtained for a given gel height by optimizing the composition of the gel matrix through the use of an incremental pre-formulation method of gel gradient casting.

Prior to this invention, the previous technology for gradient gel casting and uniform matrix gel casting involved the introduction of reactive acrylamide or related (vinyl) monomer solutions into a casting cassette or space that is sealed on the sides and the bottoms. The polymerization reaction proceeds in one or more batch compartments by chemically initiated or photo-initiated radical chain polymerization. Temporally varying the composition of one or more components of the reactive mixture gradient allows for the creation of a vertical gradient as the solution fills the set volume space from the bottom up.

Our invention involves the introduction of many reactive acrylamide formulations through a vertical series of closely spaced nozzles along one side of a closed continuously moving, casting manifold composed of two belts. These two belts seal together at the top and bottom and pull apart at the opposite end of the continuous casting manifold after polymerization is complete. Compositional variation is achieved by pre-formulating each nozzles output instead of the standard method of mixing varying percentages of two or more limiting compositions.

This method of creating a gradient with a large number of incremental formulations provides unprecedented control over the vertical distribution of multiple reaction components with exceptional reproducibility for as many gels as one chooses to produce. Among the components of the reaction mix that can be optimized for each increment are the monomer concentration, the cross-linker ratio, initiator or chain-transfer reagents and solvent/denaturant components.

An issue that is introduced with this method involves the vertical spacing and number of incremental formulations that are required so as not to introduce stair-step artifacts in the resulting polymer gradient. We must optimize this parameter by balancing polymerization reaction kinetics and free diffusion between adjacent increments prior to gelation.

Next, it is necessary to determine the spacing and number of incremental gradient compositions needed to eliminate systematic resolution artifacts within the overall gel matrix gradient.

In single composition (non-gradient) acrylamide gels the kinetics of polymerization are uniform throughout the gel and are dependent on several physical and chemical parameters such as temperature, monomer concentration and initiation conditions. The rate of polymerization for free radical polymerization reactions is given by $$R_P = k_P[M](R_i/2k_t)^{1/2} \tag{1-1}$$

where $R_i$ and $R_P$ are the rates of initiation and propagation, respectively and $k_P$ and $k_t$ are the rate constants for propagation and termination. The rate of propagation ($R_p$) is a good approximation of the rate of polymerization. [M] is the concentration of monomer. This relationship holds under the steady state assumption where the concentration of radicals rapidly reaches a constant value. All of these constants are dependent on temperature and the initiation rate is dependent on initiator concentration and/or quantum yield and intensity in the case of photo-initiated free radical polymerization, the matter being the methods of choice for our continuous casting process. Odien, G., Principles of Polymerization 3$^{rd}$ Ed. John F. Wiley & Sons Inc. (1991).

TABLE 1

Rates of conversion of Acrylamide/Bis-acrylamide to polymer with temperature and Riboflavin photo-initiator concentration
−6% T 4%C [initial monomer]

| Temperature ° C. | Time (hours) | [Riboflavin] $\mu$M | Percent Conversion |
|---|---|---|---|
| 25 | 1 | 1.16 | 70% |
| 25 | 1 | 1.75 | 70% |
| 25 | 1 | 2.32 | 73% |
| 25 | 2 | 1.16 | 78% |
| 25 | 4 | 1.16 | 86% |
| 25 | 8 | 1.16 | 94% |
| 50 | 1 | 1.16 | 76% |
| 50 | 1 | 1.75 | 84% |
| 50 | 1 | 2.32 | 88% |
| 50 | 2 | 1.16 | 83% |
| 50 | 4 | 1.16 | 88% |
| 50 | 8 | 1.16 | 93% |
| 70 | 1 | 1.16 | 84% |
| 70 | 1 | 1.75 | 88% |
| 70 | 1 | 2.32 | 92% |
| 70 | 2 | 1.16 | 91% |
| 70 | 4 | 1.16 | 92% |
| 70 | 8 | 1.16 | 93% |

Since the concentration of acrylamide gel reactants varies with location in a gradient gel, the kinetics and heats of reaction also vary. Unless carefully controlled, this will result in uneven polymerization rates with concomitant variation in gel charcteristics such a kinetic chain length and cross-linker distribution. Additionally, the possibility of positive feedback loops between temperature and reaction rate can, under some conditions, cause convective distortions in a gel gradient and a complete loss of repoducibility.

It is, therefore, desired to maintain the polymerization rate constant across variable concentration acrylamide gel gradients by varying the temperature, initiator concentration or photo-intensity in a compensatory gradient. Our unique approach to casting provides, in addition to the aforementioned incremental composition formulation options, the ability to vary the temperature and UV light intensity both vertically and horizontally (as the polymerizing gel moves along the continuous casting belt).

It is necessary to determine conditions that allow a polymerization time that matches the diffusion time of reaction components over a series of nozzle spacing such that the DNA fragment pattern in a sample ladder is indistinguishable from that on an equivalent continuously cast gradient under similar conditions.

EXAMPLE 3
Construction of a Small Scale Laboratory Apparatus to Model the Effect of Nozzle Number and Spacing on Continuously Cast DNA Sequencing Acrylamide Slab Gels An experimental gel casting device is constructed, primarily of plastic. This device may be used with subsequent modifications for all of the gel casting experiments. For most applications, the device will contain unreacted solutions in a vertical series of trays at one side of a sealed casting box. Each tray will consist of a thin rigid plate for the base and an elastomeric gasket/spacer with a narrow outlet at one side. The thickness of these gasket/spacers, which will be stacked together, will vary from one experiment to the next in order to vary the center spacing and number of gel formulations. A means of venting the enclosed space in each tray is provided at the opposite end from the outlet.

The entire stack of trays is placed along one side, inside an acrylic casting box, approximately 45 cm high, 100–120 cm in width and approximately 5 cm front to back. This casting box has a removable front face to access the finished gel after polymerization is complete and a removable sealing cover to control the pressure within the casting space. In addition the box has an adjustable position rigid pressure plate inside that is attached to the back face of the box with a series of screws that can adjust the plate towards the front and back in order to determine the thickness of the laminar casting space. The removable front face is transparent to long wavelength UV illumination for photo-initiation of polymerization.

The side of the casting box opposite the stack of trays has a vertical slot that corresponds to the cross-section of the laminar gel casting space. A spacer plate that is selected to have a vertical height, width and thickness equivalent to the finished gel is inserted through this slot and pulled up to the outlets at the stack of trays. The purpose of this spacer plate is to fill the casting space prior to the introduction of the polymer reaction mix. As the plate is pulled out to the side the polymer reaction mix fills the space and displaces the spacer plate.

This somewhat unusual arrangement for filling a laminar casting space serves a dual purpose. First, it is designed to mimic the arrangement in the large scale continuous casting method and it allows the determination of nozzle spacing and nozzle number. It also allows for experimentation with coordinated reaction casting method two belts consisting of 0.5–3 mil polyester sheets are attached to the inside end of the removable spacer plate so that they are drawn off a roll and pressed against the rigid sides of the laminar space by the internal pressure of the reaction mix as the spacer plate is pulled out to the side. This provision thus mimics the continuous belt used in the gel casting machine of the invention.

EXAMPLE 4
Determination of Reaction Rates Under Experimental Conditions as a Function of Reagent Concentrations, Additives and Radical Chain Initiator Levels and Temperature A multiple factorial analysis of the polymerization reaction rate is determined for the formulations and conditions that will be used in our subsequent experiments. There are several standard physiochemical methods of directly determining $R_P$ for chain polymerization that depend on differences between the properties of the monomer and the polymer states such as refractive index, density, spectral absorption and solubility.

One of the most widely used and useful methods of monitoring polymerization rate over the entire reaction coordinate involves dilatometry. Dilatometry measures changes in volume of the reaction mixture using a thin calibrated neck above a closed vessel. We will monitor our polymerization reactions using a special spacer/comb combination for a standard mini-gel cassette that has a closed top. A calibrated micropipet is inserted as a vertical vent. This will allow us to maintain a constant temperature (bath) and UV illumination intensity as we measure $R_P$ directly.

A more functional measure of polymerization is available for aqueous network polymers such as cross-linked acrylamide gel that is particularly useful for our application where we are matching diffusion rate to polymerization rate approximated by the "gelation" point. The gelation point can be determined by measuring the time dependence of the viscosity of the reaction solution. Diffusion of stepwise artifacts in our multiple formulation approach will be directly limited by this viscosity increase so it is a practical parameter to measure.

One method of measuring viscosity uses a standard polymer characterization differential viscometer such as the Viscotek model 150 differential viscometer. This instrument will allow characterization of molecular size (chain length) and polymer branching as well as reaction rate.

EXAMPLE 5
Analysis of the Number of Nozzles and Spacing Required to Prevent Stair-step Artifacts in Full Height Gels Once the gelation rate is determined for various physiochemical parameters the next step is to cast gradient gels using a series of nozzle spacing with the apparatus described in above. The linearity and variation in gel concentration and pore size across the gradient for various formulations will be determined. An optimal spacing for each gelation time will be calibrated. It is then possible to directly analyze total monomer conversion and points for excised gel fractions by weighing dehydrated gel fragments and wash fractions. Then DNA size standards run on the apparatus are compared against similar gradients generated using conventional gradient mixing technology. These fluorescent labels DNA sequencing test gels are analyzed using a Molecular Dynamics, Inc. FluorImager 595. The images are compared for uniformity of fragment spacing using the Image Quant® software supplied with the FluorImager. Following linear gradients the apparatus is tested using complex gradients that vary in composition exponentially or sigmoidally. Gradient slopes equal to the maximum slope projected for DNA analysis are tested for the worst case scenario of diffusion limited smoothing of the slope. Nozzle spacing and gelation rate are chosen to use in the optimization of DNA sequencing spacing and resolution as described below Determination of gradient conditions that optimize the resolution, spacing and read-length of DNA sequencing fragments in polyacrylamide sequencing gels.

In the Sangar (dideoxy) method of DNA sequencing single strand chain terminated fragments are typically separated by size in a denaturing 6–8M urea 4.506.0% non gradient acrylamide gel from 43 to 62 cm high using a TBE buffer. This non-gradient formulation results in the smallest (fastest running) chain terminated fragments at the bottom of the gel spaced widely compared to the bands at the top of the gel. This pattern results in less than optimal information density for a given length of gel. In order to overcome spacing problems and increase efficiency, a series of incremental gradient compositions are formulated that provide for an even spacing and bandwidth for as many chain terminated fragments as is possible for a given gel dimension.

EXAMPLE 6
Determination of Optimal Spacing for Various Gel Lengths by Measuring Fragment Mobility with Time Using Photopolymerized Exponential or Sigmoidal Acrylamide Concentration Gradients Using the apparatus described above one optimized for increment number, either exponential of sigmoidal concentration differential formulation will be premixed with counter gradients of initiators or chain transfer reagents to give constant polymerization rates. These differential formulations are preloaded into the trays described above and drawn into the casting chamber by sliding out the spacer plate. The gel is exposed to UV illumination levels previously determined and allowed to harden for up to 2 hours to ensure complete polymerization.

Following polymerization, the cast gel is mounted on an aluminum backed vertical sequencing system such as the Owl Scientific model #S3S. Fluorescent DNA size marker standards such as the Pharmacia Biotech ALF markers are loaded and separated to provide evenly spaced mobility markers. The fluorescent images are read as before using a Molecular Dynamics FluorImager 595. Mobility plots vs. molecular size are determined for each sigmoidal gradient condition.

EXAMPLE 7
Determination of Resolution at Various Gel Positions (Read Length) by Imaging Test Dideoxy Sequencing Samples in Separate Lanes for Various Sigmoidal Acrylamide Concentration Gradients Using several conditions optimized in the above mobility analysis, complete fluorescently labeled DNA samples and gel imaging are used across the entire plate to determine baseline and non-baseline separation limits. High resolution imaging (50 micron pixel size) on the FluorImager allows calculation of the peak width and positional overlap of the individual bands over the entire width of a lane. This results in an estimate of the resolution and read length possible for future continuous gel processing platform, where four fluorophore labeling in a single lane is used.

EXAMPLE 8
Determination of the Effect of Denaturant Gradients and Other Variables on the Resolution at Various Positions Along the Gel Additional component gradient formulations that vary the denaturant concentration independently of the acrylamide concentration gradient are run and analyzed as shown above using complete fluorescently labeled samples and imaging. This allows for the determination of the optimal denaturant concentration as a function of read length for each concentration gradient studied.

Limits of Cast Gel Thickness

The apparatus described above has several aspects of the design elaborated here including the use of two exceptionally flat, rigid platens within the casting box. One of these platens is the fixed and UV transparent face of the casting box. The other platen is mounted inside and against the back face of the casting box. This platen is mounted at multiple points with fine lateral control so as to create a laminar gel space thickness adjustable between varying thickness with less than 5% variation in flatness over the platen face. The thickness of the spacer plate is matched to the width of the casting space as adjusted.

Determination and calibration of the deflection of the platens under carrying internal gel reaction mix pressures.

The next step is to determine the minimum pressure required to hold the flexible Mylar® belt against the rigid platens and adjust the platens to compensate for this pressure during the polymerization reaction.

EXAMPLE 9
Calibration of Flatness of Casting Space as Function of Internal Pressure Using the apparatus described above, the next step is to adjust the nominal width of the gel casting space. The casting space is then pressurized with distilled water to various pressure levels below 1 atmosphere. The plate deflection is measured to 1 micrometer or less under the pressurized conditions across the entire platen face.

Next, calculation of a deflection pre-loading for each point that compensates for a specific fluid pressure. With this pre loaded stress in place, the specific pressure is reapplied and deflection is measured again. This process is repeated until the deflection is exactly compensated at a given pressure. The calibration data is recorded for use in subsequent gel polymerization experiments.

The issue of the calibration of flatness is relatively minor for the small scale device described above. In any subsequent production versions of the device the rigid platens are constructed as is required to eliminate defection altogether as a constraint.

Determining the uniformity of polyacrylamide gel thickness for various nominal thickness values by direct measurement of the finished gel There are many factors that could affect the thickness of a fully polymerized gel other than the shape of the casting space. These include physiochemical inhomogeneities such as endo-osmotic swelling due to the gel electrolyte distribution. A completed gel is quite compressible mechanically and therefore its thickness is hard to measure by direct means. The next step is to map variations in the gel thickness across the entire face of the gel using several scales of measurement by very carefully excising the completed gel in a two dimensional grid of segments. These segments are analyzed by total weight and acrylamide composition.

EXAMPLE 10
Excision of Polymerized Gels for Grid Analysis on Several Scales in Two Dimensions A frame that holds cutting blades in a grid pattern at exact spacing (approximately 1 cm to 5 cm) on center is constructed. This frame cuts a completed gel into exact dimension pieces. These pieces are carefully excised for analysis. The casting and fractionation of the test gels is performed in a low particular laminar flow environment to prevent contamination. This space is humidity controlled just below 100% to prevent condensation or evaporation from gel surface.

EXAMPLE 11
Direct Analysis of Gel Fractions From the Grid For Thickness and Composition The excised gel grid fractions are weighed using a semi-micro analytical balance that is temperature and humidity controlled in a low particulate hood. The distribution of grid fraction weights are proportional to the variations in thickness of the gel. This distribution is determined for multiple replicate gels at several grid sizes. The variation in thickness is determined at several nominal gel thicknesses.

In addition to gel thickness variations, each excised grid fraction is thoroughly washed in distilled water to remove any low molecular weight components and lyophilized to remove all traces of water. The residue gel weight is recorded. Comparison of the pattern of variation between hydrated gel grid fractions and the pattern of variation in the residual (dry) gel weights will normalize and verify that the hydrated gel weights reflect true differences in the thickness of the gel fraction and not variations in composition.

This uniformity analysis determines the limitation of minimum gel thickness for the continuously cast gel process, and therefore the level of coulombic heating, that can be tolerated without distortion of the DNA sequencing gel from excessive heating.

We claim:
1. An apparatus for the continuous casting of gels comprising:
   a) a means of introducing into a molding space a reaction mixture capable of becoming a gel, wherein said means of introducing into the molding space the reaction mixture, comprises at least one incremental formulation reservoir that delivers pre-formulated reaction mixture solution through an equal number of nozzles into one vertical edge of said molding space in order to create predetermined gradient conditions, and said reaction mixture solution is delivered to a sealed molding space from at least one incremental formulation reservoir at one vertical edge of the molding space;
   b) a casting manifold enclosing said molding space and said casting manifold providing a means of creating a continuously moving, sealed molding space for maintaining said reaction mixture during a gelation process;
   c) a means for formulating a vertical gradient of composition in a plurality of components within said reaction mixture as said reaction mixture enters said molding space by pre-formulating a composition of an incremental reaction mix formula;
   d) a venting means to displace air entrained in the reaction mixture within the molding space;
   e) a means of initiation of a polymerization process as said reaction mixture enters said molding space;
   f) a means of controlling the temperature of the reaction mixture during the gelation process as the reaction mixture travels through the apparatus;
   g) a means for removing a polymerized gel from the molding space;
   h) a means for cutting the gel to a desired length;
   i) a means for removing excess gel formed during the process; and
   j) a means for stacking the polymerized, cut gels.

2. The apparatus of claim 1, wherein, said means of introducing into the molding space the reaction mixture comprises a multi-chamber cylinder block and pistons, which allows said reaction mixture solutions to be delivered in a controlled and uniform rate.

3. The apparatus of claim 2, wherein said multi-chamber cylinder block and pistons further comprises:
   a) a series of layered metal, plastic or other composite laminations having an array of aligned holes that when laminated together vertically, define a plurality of vertical cylinders or cylindrical spaces when stacked together;
   b) said plurality of cylinders having an inlet end and an outlet end, and each cylinder having a tight fitting glass or plastic column sleeve inserted with O-ring seals at the inlet and outlet end of said column, and which terminate at the end of the cylinder and close the cylinder against a specific inlet and outlet layer of said multi-chamber cylinder block so that it defines a primary reservoir, said primary reservoirs terminating in individual pairs of one inlet and one outlet layer of said multi-chamber cylinder block, and each primary reservoir is provided at least one nozzle at the molding space and a horizontal channel in said outlet layer that defines an outlet channel, and at least one piston is disposed within each primary reservoir and separates the primary reservoirs into an inlet and an outlet chamber such that said reaction mix formula resides within the outlet chamber connected to the outlet channel, and a horizontal inlet channel is provided in said inlet layer of each reservoir so that they connectively attach each primary reservoir to a common inlet channel in order to provide a positive hydraulic pressure, and within said common inlet chamber is a drive fluid and said inlet chamber is connected to a common pump that supplies a uniform pressure to all of the primary reservoirs and a uniform flow rate for each primary reservoir;

c) the primary reservoirs in said multi-chamber cylinder block are arranged such that those incremental formulation reservoirs that supply reaction mix formula to a topmost one-half of said molding space are arranged so that their inlet ends are above said molding space and those incremental formulation reservoirs that supply reaction mix formula to a lowermost one-half of said molding space are arranged so that their inlet ends are below said molding space; and d) a means of calibrating and adjusting a plurality of relative flow rates between primary reservoirs in order to keep all incremental reaction mix formulation flow rates and overall volumes equivalent over the entire production run.

4. The apparatus of claim 3, wherein said means of calibrating and adjusting the relative flow rates between primary reservoirs comprises:

a) an orifice plate positioned at the horizontal outlet layer of each primary reservoir and disposed between said outlet chamber of said primary reservoir and said horizontal outlet layer;

b) said orifice plate having at least three distinct laminated layers such that an outer two layers of said orifice plate are comprised of rigid materials selected from metal, or plastic or other laminate, and a middle layer of said orifice plate is comprised of a compressible elastomeric material;

c) a plurality of transversing channels penetrating at least two layers of said orifice plate and where one of the penetrated layers being said middle layer, thereby connecting said outlet chamber of said primary reservoir to said horizontal outlet channel;

d) a screw-cap means positioned at the horizontal inlet layer for each primary reservoir and disposed between an inlet chamber of said primary reservoir and said horizontal inlet channel, and connectively extending through said horizontal inlet layer to a surface of said multi-chamber cylinder block such that said screw-cap can be threadedly affixed to said cylinder block through the inlet layer of said cylinder block;

e) said screw-cap means also having a plurality of transverse channels connecting said inlet chamber of said primary reservoir to said horizontal inlet channel such that said plurality of transverse channels remain connected between said inlet chamber of said primary reservoir and said horizontal inlet channel as said screw-cap means is adjusted and vertically repositioned relative to said multi-chamber cylinder block;

f) a means to seal said screw-cap means between said transverse channels in said inlet layer and said multi-chamber cylinder block; and g) said screw-cap means being capable of generating a compressive force transmitted to said orifice plate and can compress said compressible elastomeric middle layer of said orifice plate.

5. The apparatus of claim 4 wherein said casting manifold comprises:

a) a cavity having two sides comprised of a plurality of flexible moving belts, a top and bottom, and an upstream and a downstream end;

b) wherein said top and bottom of said cavity are each sealed by an opposable compression roller means comprised of at least two opposed compression rollers, a lower and an upper, along a length of the top and bottom of said molding space, and having a suitable vertical width so as to form a seal under less than 1 atmosphere pressure, wherein said lower opposable compression roller supports the gel introduced into said molding space onto a secondary support means such that the secondary support means is also supported within said molding space by the opposable compression roller means;

c) said plurality of flexible moving belts having a continuous mating surface on the cavity forming face of said flexible moving belts at the top and bottom of said molding space where said opposable compression roller means seal said molding space, and are capable of being compressed closed by said opposable compression roller means to create the seal as the flexible moving belts enter a gap between a pair of rigid platens, said rigid platens are each positioned adjacent to said flexible moving belts and on the opposite side of each belt from the side which is in contact with the reaction mixture on each side of the molding space;

d) the upstream end of the casting cavity being defined by the end wherein the reaction solution is introduced into said molding space, and the downstream end of this cavity being defined by the end of the cavity where a solidifying gel hardens as it moves through the molding space, and wherein the length of the casting cavity is sufficient to provide time enough for the reaction mixture to solidify within in the molding space at a particular speed that said flexible moving belts are moving; and e) said flexible moving belts being fitted around a series of drive roller means and idling roller means which can also act as compression roller means that seal said molding space, that maintain said mated belts at a constant speed as they move downstream during a polymerization process.

6. The apparatus of claim 5, wherein said secondary support means comprises a backing selected from the group consisting of: a rigid laminate, a mask, glass, or plastic.

7. The apparatus of claim 6, wherein both rigid platens have a finely adjustable gap between them, wherein said gap does not vary in width more than an acceptable amount so that a thickness of the solidifying reaction mixture is maintained during the gelation process by opposing internal manifold pressure that opposably applies pressure to the belts against said rigid platens.

8. The apparatus of claim 7 wherein said mating surfaces of the upper and lower belts have a bead on one belt and a groove to sealingly receive the bead on the other belt in a "ziplock" style configuration.

9. The apparatus of claim 8 wherein said top and bottom of said cavity are sealed by an upper and lower belt means wherein said lower belt means supports the gel introduced into said molding space onto the secondary support means and sealing along the lateral edges of the upper and lower belts is obtained through application of pressure onto the flexible and resilient belts.

10. The apparatus of claim 9, wherein the thickness of the solidifying reaction mixture is in the range from about 0.15 mm to about 5 mm.

11. The apparatus of claim 9, wherein the thickness of the solidifying gel is about 1 mm.

12. The apparatus of claim 9, wherein said rigid platens also provide temperature control during the gelation process.

13. The apparatus of claim 12, wherein said rigid platens also provide a means for illuminating the reaction mixture with UV light during the gelation process.

14. The apparatus of claim 12, wherein said venting means further comprises a means of collecting any entrained air displaced by the reaction mixture as it flows out of holes or other cavities, in a secondary support or a mask, and within said molding space where said secondary support enters at the upstream end of said molding space, and on a side of said secondary support away from a side where the reaction mixture is introduced.

15. The apparatus of claim 14, wherein said venting means further comprises a small chamber filled with reaction mixture at a pressure that is just slightly below a pressure in the main cavity, where the reaction mixture is introduced, so that any displaceable entrained air bubbles in the reaction mixture in the molding space can be removed as they float up and collect together into an air bell means positioned adjacent to said molding space and said secondary support at a top of a cavity, said air bell means having a release valve that can vent the air as it builds up while maintaining a constant pressure within the molding space.

16. The apparatus of claim 15, wherein said venting means has a level detector means located adjacent to a small chamber, and said level detector means maintains the air/liquid interface at a predetermined level by releasing air out the top of the collector chamber through a release valve.

17. The apparatus of claim 16, wherein said level detector means is designed with an adjustable "dead-band" or hysteresis in the level of response to filter out short term variation in flow rate.

18. The apparatus of claim 16, wherein said wherein said means of initiation of the polymerization process is through a means of chemical generation of free radicals, wherein said chemical generation means further comprises:
    a) a series of layered metal, plastic or other composite laminations having an array of aligned holes that when laminated together vertically, define a plurality of vertical cylinders or cylindrical spaces when stacked together;
    b) said plurality of cylinders having an inlet and an outlet end, and each cylinder having a tight fitting glass or plastic column sleeve inserted with O-ring seals at the inlet and outlet end of said column, and which terminate at the end of the cylinder and close the cylinder against a specific inlet and outlet layer of said multi-chamber cylinder block so that it defines a primary reservoir, said primary reservoirs terminating in individual pairs of one inlet and one outlet layer of said multi-chamber cylinder block, and each primary reservoir is provided at least one nozzle at the molding space and a horizontal channel in said outlet layer that defines an outlet channel, and at least one piston is disposed within each primary reservoir and separates the primary reservoirs into an inlet and an outlet chamber such that said reaction mix formula resides within the outlet chamber connected to the outlet channel, and a horizontal inlet channel is provided in said inlet layer of each reservoir so that they connectively attach each primary reservoir to a common inlet channel in order to provide a positive hydraulic pressure, and within said common inlet chamber is a drive fluid and said inlet chamber is connected to a common pump that supplies a uniform pressure to all of the primary reservoirs and a uniform flow rate for each primary reservoir;
    c) the primary reservoirs in said multi-chamber cylinder block are arranged such that those incremental formulation reservoirs that supply reaction mix formula to a topmost one-half of said molding space are arranged so that their inlet ends are above said molding space and those incremental formulation reservoirs that supply reaction mix formula to a lowermost one-half of said molding space are arranged so that their inlet ends are below said molding space; and
    d) a means of calibrating and adjusting a plurality of relative flow rates between primary reservoirs in order to keep all incremental reaction mix formulation flow rates and overall volumes equivalent over the entire production run.

19. The apparatus of claim 18, wherein said means of calibrating and adjusting the relative flow rates between primary reservoirs comprises:
    a) an orifice plate positioned at the horizontal outlet layer of each primary reservoir and disposed between said outlet chamber of said primary reservoir and said horizontal outlet layer;
    b) said orifice plate having at least three distinct laminated layers such that an outer two layers of said orifice plate are comprised of rigid materials selected from metal, or plastic or other laminate, and a middle layer of said orifice plate is comprised of a compressible elastomeric material;
    c) a plurality of transversing channels penetrating at least two layers of said orifice plate and where one of the penetrated layers being said middle layer, thereby connecting said outlet chamber of said primary reservoir to said horizontal outlet channel;
    d) a screw-cap means positioned at the horizontal inlet layer for each primary reservoir and disposed between an inlet chamber of said primary reservoir and said horizontal inlet channel, and connectively extending through said horizontal inlet layer to a surface of said multi-chamber cylinder block such that said screw-cap can be threadedly affixed to said cylinder block through the inlet layer of said cylinder block;
    e) said screw-cap means also having a plurality of transverse channels connecting said inlet chamber of said primary reservoir to said horizontal inlet channel such that said plurality of transverse channels remain connected between said inlet chamber of said primary reservoir and said horizontal inlet channel as said screw-cap means is adjusted and vertically repositioned relative to said multi-chamber cylinder block;
    f) a means to seal said screw-cap means between said transverse channels in said inlet layer and said multi-chamber cylinder block; and
    g) said screw-cap means being capable of generating a compressive force transmitted to said orifice plate and can compress said compressible elastomeric middle layer of said orifice plate.

20. The apparatus of claim 19, wherein said chemical generation means further comprises:
    a) a series of layered plastic or other composite laminations having an array of aligned holes that when laminated together vertically, define vertical a plurality of cylindrical spaces or cylinders when stacked together;
    b) said plurality of cylinders having a inlet and outlet end, and each cylinder having a tight fitting glass or plastic column sleeve inserted with O-ring seals at an inlet and an outlet end of said column, and which terminate at the end of the cylinder and close the cylinder against a specific inlet and outlet layer of a multi-chamber cylinder block so that it defines a primary reservoir, said primary reservoirs terminating in individual pairs of one inlet and one outlet layer of said multi-chamber cylinder block, and each primary reservoir is provided at least one nozzle at the molding space and a horizontal channel in said outlet layer that defines an outlet channel, and at least one piston is disposed within each primary reservoir and separates the primary reservoirs into an inlet and an outlet chamber such that said reaction mix formula resides within the outlet chamber connected to the outlet channel, and a horizontal inlet channel is provided in said inlet layer of each reservoir so that they connectively attach each primary reservoir to a common inlet channel in order to provide a positive hydraulic pressure, and within said inlet chamber is a drive fluid and said inlet chamber is connected to a common pump that supplies a uniform pressure to all of the primary reservoirs and a uniform flow rate for each primary reservoir;

c) a secondary reservoir having a diameter that is less than about ⅔ of a diameter of the primary reservoir;

d) said secondary reservoir positioned concentrically within the primary reservoir so that the primary glass column and a secondary glass column both have top ends terminating in adjacent multi-layer cylinder block layers and both having outlet channels terminating in the same cylinder block layer;

e) said primary and secondary glass columns both having spacer rings disposed between said primary and secondary glass columns and between the primary glass column and the cylinder block;

f) said cylinder block layers are separated by a gasket means having disposed within said gasket means, horizontal channels connecting said primary and secondary reservoir contents to a nozzle;

g) said cylinder block layers also having a circular opening in which a removable concentric orifice ring means and removable concentric orifice plate means disposed within said circular opening; and h) said removable orifice ring means and removable orifice plate means having within both a set of orifice openings which allow flow of reaction mixture from both the primary and secondary reservoirs to mix at right angles in close proximity to each other.

21. The apparatus of claim 20, wherein said removable orifice ring means and removable orifice plate means further comprise:

a) a three-layer orifice plate means having a lamination of two outer layers of a high rigidity material and a compressible elastomeric inner layer;

b) a means of applying a vertically oriented compressive force to said primary and secondary glass columns;

c) said vertically oriented compressive force being generated by an inner and an outer compression means positioned at a top of said glass columns in a terminating layer; and d) said terminating layer also having a sealing means disposed between a plurality of drive fluid manifolds and said inner and an outer compression means to provide flow control.

22. The apparatus of claim 21, wherein said means of applying a vertically oriented compressive force comprises an inner and outer compression screw means positioned at the top of said primary and secondary glass columns in said terminating layer.

23. The apparatus of claim 22, wherein said sealing means comprises a compressible ferrule means.

24. The apparatus of claim 23, wherein said secondary reservoirs have air or other gases within an inlet chamber of the same secondary reservoirs, and said air or other gases are derived from a storage tank means which is connectively attached to said horizontal inlet channels of said secondary reservoirs, and wherein the pressure of the air or other gases within the inlet chamber of same said secondary reservoirs is about equal to a hydraulic pressure of said reaction mix in said horizontal outlet channel.

25. The apparatus of claim 24, wherein said temperature controlling means comprising a front and a back platen positioned so that they enclose an upper and lower belt, and said platens positioned so that they support said upper and lower belts to provide lateral deflection resistance to a pressurized molding space, said platens having a necessary rigidity and/or UV transparency and providing for the control of reaction temperatures in the molding space.

26. The apparatus of claim 25, wherein said platens are further comprised of:

a) a plurality of plates constructed of rigid thermally conductive and relatively low expansion materials selected from aluminum, stainless steel, Pyrex glass, ceramics or other thermally conductive materials;

b) said plates are arranged to provide a heating/cooling manifold with horizontal channels allowing for a flow of a coolant, and a gasket or spacer between said plates is provided to separate these channels;

c) a vertical hot and cold coolant supply manifold positioned such that one manifold is in each of the said plates comprising the platen and a single return line in said plate that is not adjacent to said molding space;

d) at an opening between each horizontal channel and each vertical supply manifold is a manually adjustable blending valve that can be set to vary the temperature of the coolant by blending variable amounts of hot and cold coolant entering the horizontal channel;

e) said platens are fixed in place by at least one support bracket on each side, and said platens are affixed to these supports at a minimum of at least 4 locations with finely adjustable screws that allow for alignment and adjustment of a gap between the front and back platens; and f) each platen is provided with a means of connection on the lateral ends of said platen so that in can connectively attach to one or more additional platens as needed to provide the length required for a gelation time of the reaction mixture in conjunction with a belt speed.

27. The apparatus of claim 26, wherein said means for removing the polymerized gel from the mold space comprises an apparatus which unseals the lateral sides of an upper and lower belt, and then gels are cut and where supported gels are stacked by an actuated sideward shearing movement of a soft elastomeric platen located within said removal means.

28. The method of continuous casting of acrylamide or other gels for use in separations of proteins, nucleic acids or other biological materials comprising:

a) introducing into a molding space a reaction mixture comprising an reaction mixture capable of becoming a gel and initiators of its polymerization in a controlled manner, and wherein a casting manifold encloses said molding space and said casting manifold creates a continuously moving, sealed laminar cavity for maintaining a reacting gel solution at a modest pressure during a gelation process;

b) formulating a vertical gradient of composition in a plurality of components within said reaction mixture as said reaction mixture enters said molding space by pre-formulating the composition of an incremental reaction mix formula;

c) displacing air entrained in the reaction mixture within the molding space by use of a venting means disposed within said casting manifold;

d) initiating a polymerization process as said reaction mixture enters said mold space;

e) controlling a temperature of the reaction mixture during the gelation process as the reaction mixture travels through the apparatus;

f) removing a polymerized gel from the mold space, cutting the gel to a desired length, removing excess gel formed during the process, and stacking the polymerized, cut gels, further comprising:

1) a portion of the continuous gel moving into a cutting space in a cutting means;

2) said portion of the continuous gel is sheared from an upstream gel portion on a downstream side of a mold flash so that this flash will be attached to the downstream side of the next upstream gel, so that any mold flash, attached to the downstream side of the gel is cut off on the next round with this same shearing actuation at the downstream end of the gel;

3) a small extension of an actuating platen remains against the downstream shearing surface after a main platen returns in order to isolate the removed mold flash in a chamber at the extreme downstream end of the line where it can be washed away; and 4) stacking the completed gels or masks onto a washing belt or other support for further processing or stacking the completed gels or masks into running cassettes ready for use.

\* \* \* \* \*